United States Patent
Yamaguchi

(10) Patent No.: US 9,095,250 B2
(45) Date of Patent: Aug. 4, 2015

(54) ENDOSCOPE APPARATUS WITH PARTICULAR ILLUMINATION, ILLUMINATION CONTROL AND IMAGE PROCESSING

(75) Inventor: Hiroshi Yamaguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 49 days.

(21) Appl. No.: 13/305,861

(22) Filed: Nov. 29, 2011

(65) Prior Publication Data

US 2012/0157775 A1  Jun. 21, 2012

(30) Foreign Application Priority Data

Dec. 20, 2010  (JP) ................................. 2010-283381

(51) Int. Cl.
*A61B 1/04* (2006.01)
*A61B 1/06* (2006.01)
*A61B 1/00* (2006.01)
*A61B 5/1455* (2006.01)
*A61B 5/1459* (2006.01)

(52) U.S. Cl.
CPC .............. *A61B 1/00009* (2013.01); *A61B 1/063* (2013.01); *A61B 1/0638* (2013.01); *A61B 5/1459* (2013.01); *A61B 5/14551* (2013.01); *A61B 1/0653* (2013.01)

(58) Field of Classification Search
USPC ................... 600/160, 178, 180, 476; 348/65
See application file for complete search history.

(56) References Cited

U.S. PATENT DOCUMENTS

| 8,223,198 | B2 | 7/2012 | Shibasaki | |
| 2009/0247881 | A1* | 10/2009 | Maeda et al. | 600/476 |
| 2009/0306478 | A1* | 12/2009 | Mizuyoshi | 600/178 |
| 2009/0312607 | A1 | 12/2009 | Sunagawa et al. | |
| 2010/0069720 | A1* | 3/2010 | Fulghum et al. | 600/175 |
| 2010/0094136 | A1 | 4/2010 | Nakaoka et al. | |

FOREIGN PATENT DOCUMENTS

| EP | 2105090 A1 | 9/2009 |
| JP | 2002-85342 A | 3/2002 |

(Continued)

OTHER PUBLICATIONS

Japanese Office Action for Japanese Application No. 2010-283381 dated Nov. 27, 2012, with English translation.

(Continued)

*Primary Examiner* — Anhtuan T Nguyen
*Assistant Examiner* — Aaron B Fairchild
(74) *Attorney, Agent, or Firm* — Birch, Stewart, Kolasch & Birch, LLP

(57) ABSTRACT

The endoscope apparatus includes a wavelength switching unit for switching emission wavelengths of a first illumination light including at least broadband light and a second illumination light including only plural kinds of narrowband light, an imaging unit for capturing an image of a subject by the first illumination light or the second illumination light having the switched emission wavelength in each imaging frame, an acquisition unit for acquiring biological information relating to form and/or function of a biological object serving as the subject and a mode switching unit for switching at least two diagnosis modes based on the biological information. The number of imaging frames by the imaging unit in which the emission wavelengths of the first and second illumination light are switched varies depending on the diagnosis mode.

13 Claims, 14 Drawing Sheets

(56) References Cited

FOREIGN PATENT DOCUMENTS

| | | |
|---|---|---|
| JP | 2003-93336 A | 4/2003 |
| JP | 2008-22890 A | 2/2008 |
| JP | 2008-161550 A | 7/2008 |
| JP | 2009-240516 A | 10/2009 |
| JP | 2009-279150 A | 10/2009 |
| JP | 2009-297311 A | 12/2009 |

OTHER PUBLICATIONS

Extended European Search Report dated May 22, 2012 for European Application No. 11190960.2.

Japanese Office Action for Japanese Application No. 2010-283381, dated Mar. 19, 2013, with partial English translation.

* cited by examiner

ENDOSCOPE APPARATUS WITH PARTICULAR ILLUMINATION, ILLUMINATION CONTROL AND IMAGE PROCESSING

BACKGROUND OF THE INVENTION

The present invention relates to an endoscope apparatus capable of obtaining a smooth diagnostic image suitable for observation at a high frame rate at the time of screening diagnosis and obtaining a high-definition diagnostic image at the time of detailed diagnosis by switching and using a plurality of kinds of illumination depending on purposes, such as screening diagnosis (observation) and detailed diagnosis (observation).

In diagnostic imaging using an endoscope, screening observation/inspection or screening diagnosis is performed in which cancer of a body cavity, particularly, the focus site of early-stage cancer, a lesion site, or an abnormal site, such as a hemorrhage, is observed accurately, precisely, and in detail, and prior to detailed observation for diagnosis or detailed diagnosis, a site suspected of abnormality is found from each site in a wide range of the body cavity.

In screening observation/diagnosis using the endoscope, it is necessary to observe and diagnose a wide range of the body cavity. For this reason, as observation/diagnostic images, it is necessary to observe and diagnose the wide range from a distance while moving inside the body cavity, and there is demand for bright images or smooth video (motion images).

In detailed observation/diagnosis by an endoscope, when the site suspected of abnormality found in the screening observation/diagnosis is approached, it is necessary to accurately diagnose whether or not the relevant site is an abnormal site, such as cancer. For this reason, with regard to observation/diagnostic images, it is necessary to observe and diagnose the relevant site being substantially fixed in a close contact or enlarged state, or to perceive biological changes in a plurality of features of the relevant site, and there is demand for obtaining a plurality of images using light having various wavelengths.

For this reason, screening observation/diagnosis (hereinafter, collectively called diagnosis) is generally performed by normal light observation by normal white illumination light, and detailed diagnosis is generally performed by special light observation of an enlarged target site. As special light observation, the following observation is performed: narrowband light observation in which light (narrowband light) in a narrow wavelength band having a specific center wavelength is irradiated onto the mucosal tissue of the biological object using the fact that the invasion depth of light in the depth direction with respect to a biological tissue depends on the wavelength of light, and tissue information at a desired depth of a biological tissue, particularly, information on the form of a blood vessel at a predetermined depth (surface layer blood vessel (blue: B), intermediate layer blood vessel (green: G), deep layer blood vessel (red: R), or the like) are obtained to determine the presence/absence of a focus, such as a cancer tissue; narrowband light observation in which narrowband light in the B region is irradiated onto a biological tissue using the absorbance of hemoglobin and the oxygen saturation in blood is measured; infrared light observation in which near-infrared light is irradiated onto a biological tissue using the absorbance of hemoglobin or the absorbance of ICG (indocyanine green) to be bound to protein and the oxygen saturation in blood is measured to image a blood vessel; or fluorescent observation in which the presence/absence of a focus, such as cancer cells, is diagnosed using autogenous fluorescence generated from a biological tissue, onto which excitation light in a specific narrow wavelength band is irradiated or fluorescence generated from a fluorescent medication dispersed in a specific focus, such as cancer cells, in a biological tissue.

Patent Document 1 describes an endoscope apparatus for enlarged observation in which the magnification of a subject image is variable by a remote operation. In this endoscope apparatus, an objective lens optical system which can perform normal observation and a confocal optical system which can obtain an enlarged microscopic image of a subject are provided together at the tip of an insertion portion. A video processor and a main monitor for the objective lens optical system, and a confocal image processor and a confocal image monitor for the confocal optical system are separately provided.

In the endoscope apparatus for enlarged observation described in Patent Document 1, normal white illumination light which is emitted from a light source lamp in the video processor and enters the objective lens optical system is irradiated toward a subject, reflected light from the subject is received by a solid-state imaging element to perform imaging, a captured image signal is processed by a video signal processing circuit in the video processor, and a captured subject image is displayed on the main monitor. In this way, screening by normal observation is performed. In this screening, if a site suspected of abnormality is found, the remote operation of the objective lens optical system is performed to enlarge the magnification of the subject image of the relevant site to the enlargement magnification of the confocal optical system, and the enlarged image is displayed on the main monitor. Thereafter, in the confocal optical system, reflected light by laser light which is emitted from a laser light source in the confocal image processor and enters the confocal optical system is received by a light-receiving element in the confocal image processor, the video signal is processed by a video signal processing circuit, and the enlarged microscopic image of the subject is displayed on the confocal monitor.

In this way, in the endoscope apparatus for enlarged observation, it is possible to perform detailed diagnosis on a enlarged microscopic image corresponding to the enlarged image of the site suspected of abnormality found in screening.

With regard to special light observation, Patent Document 2 describes an endoscope system which has three observation modes including a normal light observation mode in which a reflected light image is presented, a screening fluorescent observation mode (first fluorescent observation mode) in which a fluorescence intensity image is presented, and an unmixing fluorescent observation mode (second fluorescent observation mode) in which the concentration distribution of a fluorescent medication obtained by computation from a fluorescence intensity image is presented, and can select an appropriate observation mode by a mode selector.

In this endoscope system, a white light source, such as a xenon lamp, a light source for illumination light constituted by a switching RGB color filter, and two excitation light sources constituted by semiconductor lasers which emit excitation light having different wavelengths with the peak wavelengths of 680 nm and 700 nm are used as light sources. While the insertion portion at the tip of the endoscope is inserted into a body cavity and then reaches an observation site, imaging is done in the normal light observation mode using the light source for illumination light, that is, normal screening is performed. In the normal light observation mode, a light source for illumination light is constantly turned on, reflected light by RGB frame sequential light by RGB color filters is received by the imaging element to image the observation site as a color image, and the color image of the observation site is displayed on a display unit. In this mode, the two excitation light sources are turned off. If the insertion portion at the tip of the endoscope reaches the observation site, the observation mode is switched to the screening fluorescent observation mode, such that the observation-target site is cleaned and two fluorescent probes are dispersed.

In the screening fluorescent observation mode, the light source for illumination light and one excitation light source are used, and another excitation light source is not used. When the light source for illumination light is turned on, only B illumination light is irradiated onto the observation site by the color filters and imaged by the imaging element as a reflected image (B). When one excitation light source is turned on, two kinds of fluorescence which are generated when two fluorescent probes dispersed in the observation target are excited by emitted excitation light are imaged by the imaging element including an excitation light cut filter as a fluorescent image, and are displayed on the display unit as an image in which the fluorescent image and the reflected light image overlap each other. If fluorescent is not generated, the observation mode is switched to the normal observation mode, and the insertion portion at the tip of the endoscope moves to the next observation site. If fluorescent is not generated, the observation mode is switched to the unmixing observation mode.

In the unmixing observation mode, the light source for illumination light and the two excitation light sources are used. In the same manner as described above, two kinds of fluorescent images in which a reflected light image and two kinds of fluorescence are color-mixed are acquired, concentration information of the fluorescent probes is calculated from the two kinds of fluorescent images, and displayed on the display unit to overlap the reflected light image. It is possible to diagnose the presence/absence of a cancer cell on the basis of the concentration information by the two kinds of fluorescence.

[Patent Document 1] JP 2008-22890 A
[Patent Document 2] JP 2008-161550 A

SUMMARY OF THE INVENTION

On the other hand, in the endoscope apparatus for enlarged observation described in Patent Document 1, screening is performed by normal observation using white light, and if the site suspected of abnormality is found, and the enlargement magnification by the objective lens optical system in normal observation is changed to be substantially the same as the enlargement magnification of the enlarged microscopic image. Thereafter, the enlarged microscopic image of the subject is obtained by the confocal optical system, thereby performing detailed diagnosis. However, enlarged observation is simply performed, and diagnosis of an abnormal site by special light observation is not performed.

In this apparatus, even for normal observation, it is necessary to use a complex optical system, such as an objective lens optical system, causing complexity in the structure and an increase in cost. A confocal optical system for obtaining an enlarged microscopic image should also be provided, making it impossible to slenderize the insertion portion of the endoscope, and increasing burden is imposed on the subject. A processor or a monitor corresponding to the confocal optical system should also be provided, causing complexity in the configuration and an increase in cost.

In the endoscopy system described in Patent Document 2, screening by special light observation, called fluorescent observation, is performed, and the concentration of the fluorescent medication in the observation-target site by fluorescent observation in a fluorescence-generated site found by screening is visualized, thereby performing detailed diagnosis. However, with regard to screening, bright smooth video (motion image) for observing the wide range from a distance for diagnosis while moving inside the body cavity is not acquired. Instead, observation in the normal light observation mode is performed in advance, the insertion portion at the tip of the endoscope is guided to a site to be observed, and if the insertion portion at the tip of the endoscope reaches the observation site, the observation mode is switched to the screening fluorescent observation mode, and fluorescent observation of the observation-target site is performed in an enlarged state. For this reason, in this endoscope system, since it is impossible to observe the wide range for diagnosis from a distance while moving inside the body cavity in the fluorescent observation mode, it is necessary to perform screening by fluorescent observation while switching the normal observation mode and the screening fluorescent observation mode, and the operation of the operator is troublesome.

An object of the invention is to provide an endoscope apparatus capable of switching and using a plurality of kinds of illumination depending on screening diagnosis/observation, detailed diagnosis/observation, and the like with simple configuration without causing an increase in the size of an insertion portion at the tip of an endoscope and without imposing burden on a subject, obtaining a smooth diagnostic image suitable for observation at a high frame rate in screening diagnosis, and obtaining a high-precision diagnostic image for detailed diagnosis.

An object of the present invention is to provide an endoscope apparatus comprising first illumination means for emitting first illumination light including at least broadband light; second illumination means for emitting second illumination light including only plural kinds of narrowband light; emission wavelength switching means for switching emission wavelengths of the first illumination light from the first illumination means and the second illumination light from the second illumination means; imaging means for receiving return light from a subject, onto which the first illumination light or the second illumination light having the emission wavelength switched by the emission wavelength switching means is irradiated, capturing an image for each imaging frame, and outputting an imaging signal of the image; biological information acquisition means for acquiring biological information relating to form and/or function of a biological object serving as the subject from the imaging signal captured by the imaging means; and mode switching means for switching at least two diagnosis modes based on the biological information acquired by the biological information acquisition means, wherein the number of imaging frames by the imaging means in which the emission wavelengths of the first illumination light and the second illumination light for acquiring the biological information are switched by the emission wavelength switching means varies depending on the diagnosis mode switched by the mode switching means.

Preferably, said at least two diagnosis modes include a first diagnosis mode and a second diagnosis mode, the first diagnosis mode is a frame rate preference mode in which a frame rate is given preference, the second diagnosis mode is a biological information preference mode in which the biological information is given preference, and the number of imaging frames in the first diagnosis mode is smaller than the number of imaging frames in the second diagnosis mode.

Preferably, the frame rate preference mode is a mode in which the subject is screened using the biological information, and the biological information preference mode is a mode in which the biological information of a specific site of the subject specified by the screening in the frame rate preference mode is acquired.

Preferably, in the first diagnosis mode, the subject is illuminated with only the first illumination light from the first illumination means, and the second diagnosis mode includes at least the illumination of the subject with the second illumination light from the second illumination means.

Preferably, the first illumination light emitted from the first illumination means and the second illumination light emitted from the second illumination means are emitted from different illumination openings and illuminate the subject.

Preferably, the first illumination means has two or more narrowband light sources which emit plural kinds of narrowband light having different wavelengths, and a fluorescent substance which transmits at least a part of plural kinds of narrowband light emitted from the two or more narrowband light sources, and is excited by one kind of narrowband light from one narrowband light source from among the two or more narrowband light sources to emit fluorescence, the first illumination means emits from the fluorescent substance as the broadband light synthesized light of transmitted light of the fluorescent substance by the one kind of narrowband light and the fluorescence emitted from the fluorescent substance, the first illumination light includes the synthesized light as the broadband light and one or more kinds of another narrowband light from one or more narrowband light sources from among the two or more narrowband light sources, and the second illumination means has two or more narrowband light sources which emit plural kinds of narrowband light having different wavelengths as the second illumination light.

Preferably, the first illumination means has first and second narrowband light sources which respectively emit first and second narrowband light having different wavelengths, and a fluorescent substance which transmits at least a part of the first and second narrowband light, and is excited by the first narrowband light to emit fluorescence, the first illumination means emits synthesized light of the first narrowband light having transmitted the fluorescent substance and the fluorescence emitted from the fluorescent substance excited by the first narrowband light as the broadband light, the second illumination means has three narrowband light sources which emit three kinds of narrowband light having different wavelengths, and the three narrowband light sources include the first and second narrowband light sources, and a third narrowband light source which emits third narrowband light having a wavelength different from the first and second narrowband light.

Preferably, the first narrowband light is narrowband light which has a wavelength suitable for generating pseudo white light as the broadband light when the fluorescence is excited and emitted from the fluorescent substance, the second narrowband light is narrowband light which has a wavelength suitable for acquiring oxygen saturation of blood of the biological object as the biological information, and the third narrowband light is narrowband light which has a wavelength suitable for acquiring information of a surface layer blood vessel of the biological object as the biological information.

Preferably, the first narrowband light source is a first blue laser which emits narrowband light having a wavelength in a blue region as the first narrowband light, the second narrowband light source is a second blue laser which emits narrowband light in a wavelength band from the blue region to a blue-green region longer than the emission wavelength band of the first blue laser, and the third narrowband light source is a third blue laser which emits narrowband light in a wavelength band from a blue-violet region to the blue region shorter than the emission wavelength band of the first blue laser.

Preferably, the wavelength band of the first narrowband light is 440±10 nm, the wavelength band of the second narrowband light is 470±10 nm, and the wavelength band of the third narrowband light is 400±10 nm.

Preferably, the imaging means is a color imaging element capable of separately imaging at least three wavelength bands.

Preferably, the endoscope apparatus further comprises means for generating a narrowband image signal from the imaging signal captured by the imaging means at the time of the irradiation of the broadband light onto the subject by spectral estimation.

Preferably, the biological information acquisition means computes oxygen saturation of blood of the biological object.

According to the invention, it is possible to switch and use a plurality of kinds of illumination depending on screening diagnosis/observation, detailed diagnosis/observation, and the like with simple configuration without causing an increase in the size of the insertion portion at the tip of the endoscope and without imposing burden on the subject, to obtain a smooth diagnostic image suitable for observation at a high frame rate in screening diagnosis, and to obtain a high-precision diagnostic image in detailed diagnosis. As a result, it is possible to rapidly perform accurate diagnosis or observation constantly without imposing burden on the subject.

DETAILED DESCRIPTION OF THE INVENTION

Hereinafter, an endoscope apparatus according to the invention will be described with reference to a preferred embodiment shown in the accompanying drawings.

Figure 1:
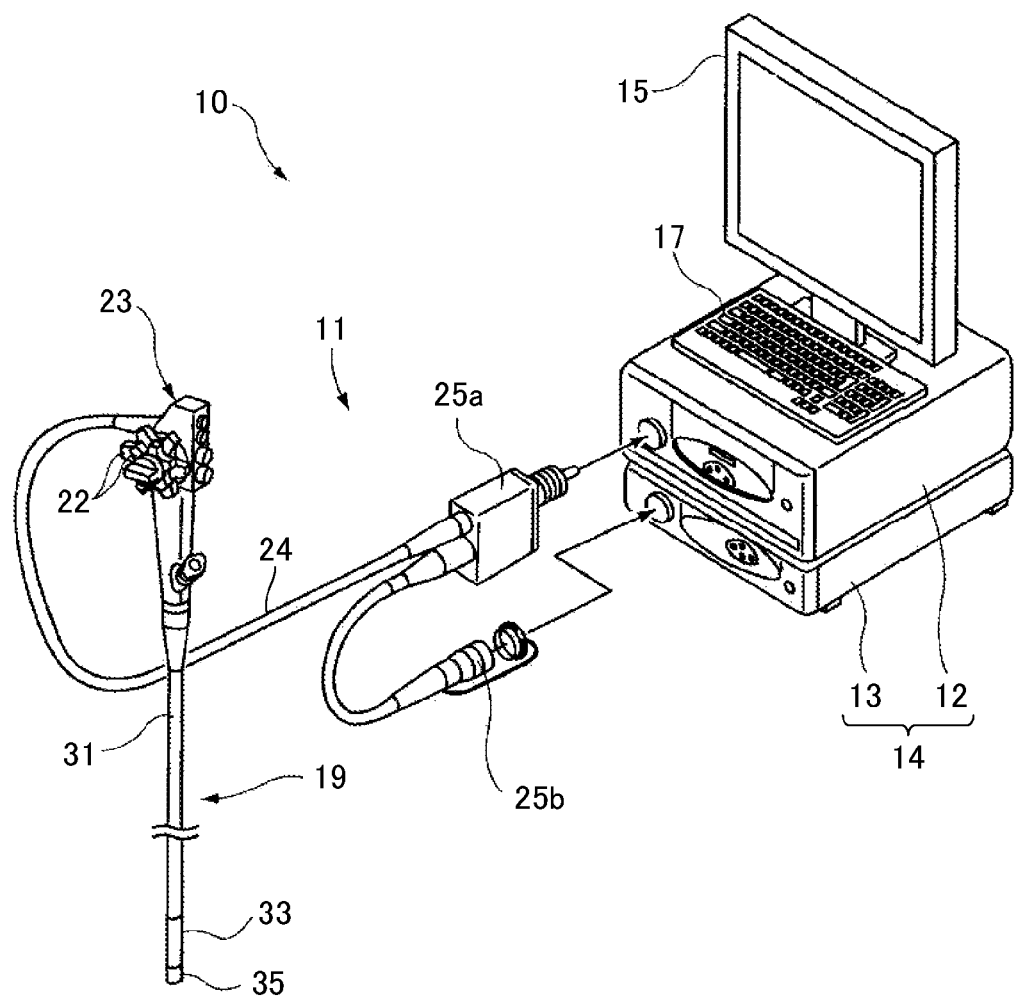
FIG. 1 is a perspective view showing the appearance of an example of an endoscope apparatus according to an embodiment of the invention.
Figure 2:
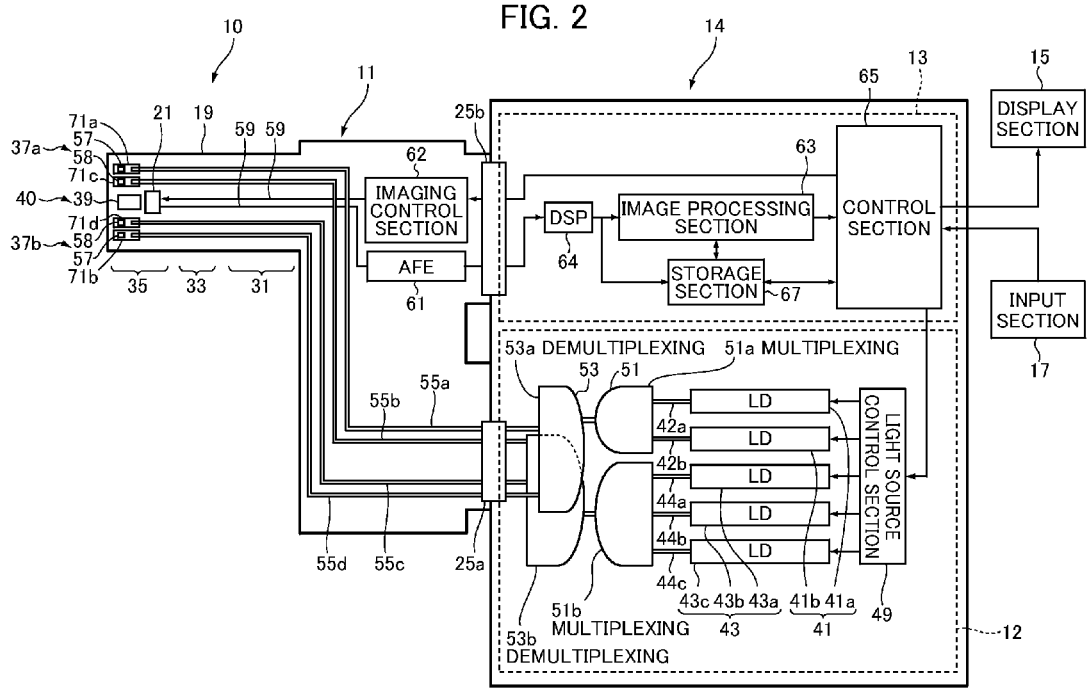
FIG. 2 is a schematic view conceptually showing the overall configuration of the endoscope apparatus shown in FIG. 1.
Figure 3:
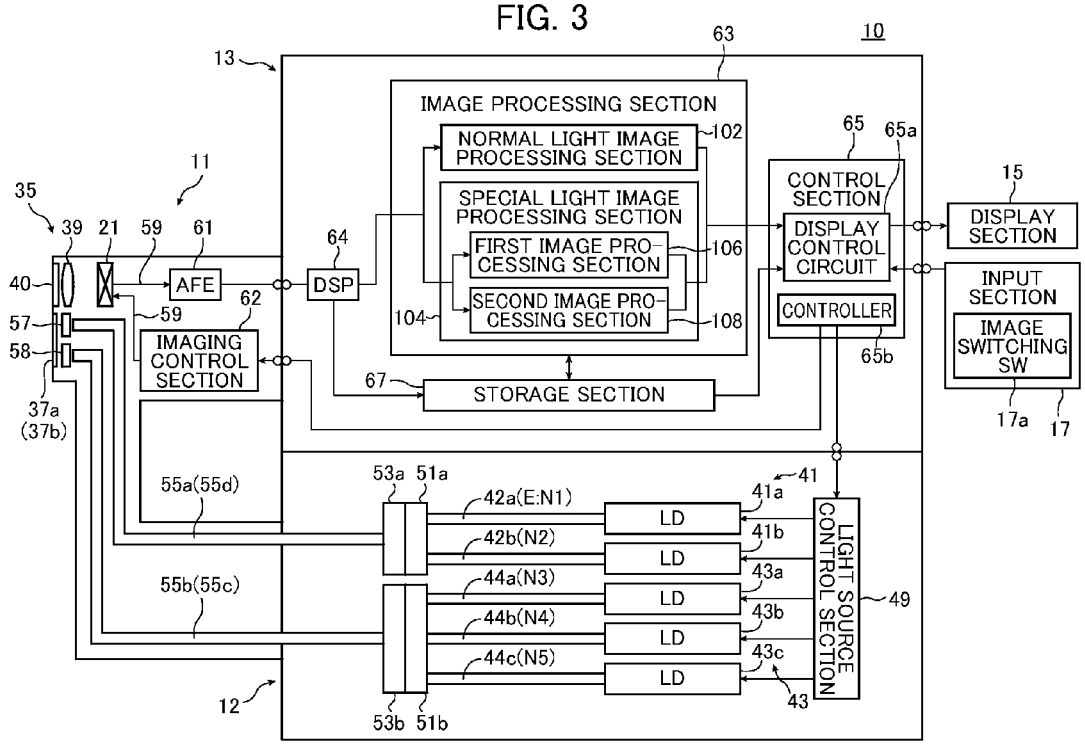
FIG. 3 is a block diagram showing the electrical configuration of the endoscope apparatus shown in FIG. 1.

FIG. 1 is a perspective view showing the appearance of an example of an endoscope apparatus according to an embodiment of the invention. FIG. 2 is a schematic view conceptually showing the overall configuration of the endoscope apparatus shown in FIG. 1. FIG. 3 is a block diagram showing the electrical configuration of the endoscope apparatus shown in FIG. 1.

As shown in FIGS. 1 and 2, an endoscope apparatus 10 of the invention is one type of medical instrument. The endoscope apparatus 10 includes an endoscope 11 which captures the inside of a body cavity of a subject, a light source device 12 which supplies light to be irradiated into body cavity for imaging, a processor 13 which generates image information of an image including biological information, such as blood vessel information of a subject tissue inside the body cavity, on the basis of an image signal obtained by imaging, a control device 14 to which the endoscope 11 is connected, a display section 15 which is constituted by a monitor for displaying image information, such as an image inside the body cavity, and an input section 17 which receives an input operation of the endoscope apparatus 10.

The endoscope apparatus 10 of the invention includes a normal observation mode (also referred to as a normal light mode), special light observation mode (also referred to as a special light mode), and the like as observation modes. The special light observation mode includes diagnosis modes including a screening diagnosis mode, that is, a frame rate preference mode of the invention, a detailed diagnosis mode, that is, a biological information preference mode of the invention, and the like.

Hereinafter, although a case where the oxygen saturation of blood of a biological object is acquired as biological information of the subject in the special light observation mode will be described as a representative example, the invention is not limited thereto, and blood vessel depth information, blood vessel size information, blood vessel set information, blood vessel shape information, blood volume information, and the like may be acquired. It should be noted that, in the special light mode, not only narrowband light observation, but also special observation, such as infrared light observation, autogenous fluorescent observation, or fluorescent observation, may be performed.

First, the endoscope 11 of this example will be described.

The endoscope 11 is an electronic endoscope having an illumination optical system which emits illumination light from the tip of the insertion portion 19 inserted into the subject, and an imaging optical system which includes an imaging element 21 (see FIG. 2) imaging a region to be observed. The endoscope 11 is optically connected to the light source device 12 and electrically connected to the processor 13. The processor 13 is electrically connected to the display section 15 and the input section 17. The input section 17 functions as a UI (user interface) which receives an input operation, such as the setting of the observation mode of the normal light mode or the special light mode or function setting.

The endoscope apparatus 10 of the invention may have a recording section (recording device) (not shown) which outputs image information or the like as a hard copy image, in addition to the display section 15.

The endoscope 11 includes a flexible insertion portion 19 which is inserted into the body cavity, an operation section 23 which is provided in the base portion of the insertion portion 19 and performs a bending operation of the tip of the insertion portion 19 or an operation for observation, a universal cord 24 which connects the operation section 17 and the control device 14, and connector portions 25a and 25b which are attached to the universal cord 24 and detachably connects the endoscope 11 to the control device 14. Though not shown, inside the operation section 23 and the insertion portion 19, various channels including a forceps channel into which a treatment tool for tissue extraction or the like is inserted, a channel for air supply/water supply, and the like are provided.

The insertion portion 19 is constituted by a flexible portion 31, a bent portion 33, and a tip portion 35. As shown in FIG. 2, the tip portion 35 has arranged therein irradiation openings 37a and 37b which irradiate illumination light by the illumination optical system onto a region to be observed, an imaging element 21 which acquires image information of the region to be observed, and an objective lens unit 39 which constitutes an imaging optical system in the light-receiving surface of the imaging element 21. The outer surface of the objective lens unit 39 constitutes an observation window 40.

The bent portion 33 is provided between the flexible portion 31 and the tip portion 35, and is bendable by a rotation operation of an angle knob 22 arranged in the operation section 23 shown in FIG. 1. The bent portion 33 can be bent in an arbitrary direction at an arbitrary angle in accordance with a site or the like of the subject in which the endoscope 11 is used, such that the irradiation openings 37a and 37b of the endoscope tip portion 35 and the observation direction of the imaging element 21 can be directed to a desired observation site.

The structure of the illumination optical system inside the endoscope 11, the electrical configuration of the imaging system, and the structure of the irradiation openings 37a and 37b of the insertion portion 19 will be described below in detail.

Next, the light source device 12 and the processor 13 in the control device 14 of this example will be described.

In the invention, the light source device 12 generates illumination light which is supplied to the irradiation openings 37a and 37b of the tip portion 35 of the endoscope 11. The processor 13 performs an image process on a captured image signal to be transmitted from the imaging element 21 of the endoscope 11 on the basis of an instruction from the operation section 23 or the input section 17 of the endoscope 11 to generate an image for display and supplies the image for display to the display section 15.

The light source device 12 has a first illumination light source section 41 which is a light source section of a system 1 and emits first illumination light including at least broadband light, a second illumination light source section 43 which is a light source section of a system 2 and emits second illumination light including only a plurality of narrowband light, and a light source control section 49 which switches the emission of each narrowband light source of the first illumination light source section 41 and the second illumination light source section 43 on the basis of an instruction according to each observation mode from the control section 65 of the processor 13 in accordance with each observation mode, and individually controls the emission amount.

The first illumination light source section 41 has at least a broadband light source. In the example of the drawing, the first illumination light source section 41 has a narrowband light source 41a which emits excitation light E as narrowband light N1 having a narrowband wavelength, a narrowband light source 41b which emits narrowband light N2 having an emission wavelength different from excitation light E, and a fluorescent substance 57 which emits fluorescence by the irradiation of excitation light E.

The combination of the narrowband light source 41a and the fluorescent substance 57 constitutes a broadband light source which emits broadband light, such as white light, including excitation light and fluorescence. In the broadband light source, when excitation light E emitted from the narrowband light source 41a is irradiated onto the fluorescent substance 57, the fluorescent substance 57 is excited by excitation light E to emit fluorescent having at least a wavelength band other than the wavelength band of excitation light E, excitation light E is transmitted, and combined light of emitted fluorescence and transmitted excitation light E is emitted as pseudo white light.

The fluorescent substance 57 emits a small amount of fluorescence by the irradiation of narrowband light N2 emitted by the narrowband light source 41b, which is smaller than the amount of fluorescence by the irradiation of excitation light E, and transmits a large amount of narrowband light N2. That is, in the combination of the narrowband light source 41b and the fluorescent substance 57, narrowband light N2 which transmits the fluorescent substance 57 is dominant. For this reason, this combination can be regarded as a narrowband light source which emits narrowband light N2.

That is, in the example of the drawing, the first illumination light emitted from the first illumination light source section 41 includes broadband light and narrowband light N2.

The second illumination light source section 43 has a plurality of narrowband light sources which have different emission wavelengths. In the example of the drawing, the second illumination light source section 43 has a narrowband light source 43a which emits narrowband light N3 having a predetermined narrowband wavelength, a narrowband light source 43b which emits narrowband light N4 having an emission wavelength different from narrowband light N3, a narrowband light source 43c which emits narrowband light N5 having an emission wavelength different from narrowband light N3 and N4. That is, in the example of the drawing, the second illumination light emitted from the second illumination light source section 43 includes only narrowband light N3, N4, and N5.

In the configuration example of this embodiment, the narrowband light source 41a excites the fluorescent substance 57 to emit fluorescence, and constitutes a broadband light source, called Micro-White (Product Name). It is preferable that the narrowband light source 41a emits blue laser light (narrowband light N1) having a limited wavelength of 440±10 nm as excitation light E, and is an LD (laser diode) having a center emission wavelength of 445 nm.

The narrowband light source 41b is a light source suitable for calculating the oxygen saturation in the blood. It is preferable that the narrowband light source 41b emits blue-green laser light (narrowband light N2) having a limited wavelength of 470±10 nm, preferably, 473 nm. It is more preferable that the narrowband light source 41b is a semiconductor laser (LD) having a center emission wavelength of 473 nm.

Similarly to the narrowband light source 41a, it is preferable that the narrowband light source 43a emits blue laser light (narrowband light N3) having a limited wavelength of 440±10 nm, preferably, 445 nm. It is more preferable that the narrowband light source 43a is an LD having a center emission wavelength of 445 nm.

Similarly to the narrowband light source 41b, the narrowband light source 43b is a light source suitable for calculating the oxygen saturation in the blood. It is preferable that the narrowband light source 43b emits blue-green light (narrowband light N4) having a limited wavelength of 470±10 nm, preferably, 473 nm. It is more preferable that the narrowband light source 43b is an LD having a center emission wavelength of 473 nm.

The narrowband light source 43c is a light source suitable for observing a surface layer blood vessel. It is preferable that the narrowband light source 43c emits blue-violet laser light (narrowband light N5) having a limited wavelength of 400±10 nm, preferably, 405 nm. It is more preferable that the narrowband light source 43c is an LD having a center emission wavelength of 405 nm.

For the narrowband light sources 41a to 41b and 43a to 43c, for example, a GaN-based semiconductor laser (laser diode), a broad-area InGaN-based laser diode, an InGaNAs-based laser diode, a GaNAs-based laser diode, and the like may be used. As the above-described light sources, a configuration using a light-emitting substance, such as a light-emitting diode, may be made.

The light source control section 49 of the light source device 12 switches the emission of the narrowband light sources 41a to 41b and 43a to 43c and controls the emission amount in accordance with each observation mode.

That is, the narrowband light sources 41a to 41b and 43a to 43c are individually subjected to dimming control by the light source control section 49 in accordance with each observation mode. The emission timing of each narrowband light source or the light quantity ratio is variable.

First, when the observation mode is the normal light mode, the light source control section 49 performs control such that only the narrowband light source 41a of the first illumination light source section 41 is turned on, and the narrowband light source 41b and the narrowband light sources 43a to 43c of the second illumination light source section 43 are turned off. That is, in the normal light mode, the narrowband light source 41a of the first illumination light source section 41 is turned on on the basis of a control signal from the light source control section 49. Thus, broadband light constituted by pseudo white light, in which excitation light E and fluorescence from the fluorescent substance 57 are synthesized, is emitted from the first illumination light source section 41 as the first illumination light.

Next, when the observation mode is the screening diagnosis mode of the special light observation mode, the light source control section 49 performs control such that the narrowband light source 41a and the narrowband light source 41b of the first illumination light source section 41 are turned on sequentially and alternately, and the narrowband light sources 43a to 43c of the second illumination light source section 43 are turned off. That is, in the screening diagnosis mode, the narrowband light sources 41a and 41b of the first illumination light source section 41 are turned on sequentially and alternately on the basis of a control signal from the light source control section 49. Thus, as described above, broadband light and narrowband light N2 are emitted sequentially and alternately from the first illumination light source section 41 as the first illumination light (see FIG. 11 described below).

When the observation mode is the detailed diagnosis mode of the special light observation mode, the light source control section 49 performs control such that the narrowband light source 41a of the first illumination light source section 41 and narrowband light sources 43a to 43c of the second illumination light source section 43 are turned on sequentially and alternately, and the narrowband light source 41b is turned off. That is, in the detailed diagnosis mode, the narrowband light source 41a of the first illumination light source section 41 and the narrowband light sources 43a, 43b, and 43c of the second illumination light source section 43 are turned on sequentially and alternately on the basis of a control signal from the light source control section 49. Thus, the above-described broadband light is emitted from the first illumination light source section 41 as the first illumination light, and narrowband light N3, N4, and N5 are emitted sequentially and alternately from the second illumination light source section 43 as the second illumination light (see FIG. 15 described below).

Excitation light E and narrowband light N2 emitted from the narrowband light sources 41a and 41b of the first illumination light source section 41 are respectively input to optical fibers 42a and 42b by a condensing lens (not shown), and transmitted to the connector portion 25a through a combiner 51a (51) serving as multiplexer and a coupler 53a (53) serving as a demultiplexer.

Narrowband light N3 to N5 emitted from the narrowband light sources 43a to 43c of the second illumination light source section 43 are respectively input to optical fibers 44a to 44c by a condensing lens (not shown), and transmitted to the connector portion 25a through a combiner 51b (51) serving as a multiplexer and a coupler 53b (53) serving as a demultiplexer. The invention is not limited thereto, and a configuration may be made in which narrowband light N1 to N5 from the narrowband light sources 41a to 41b and 43a to 43c are directly transmitted to the connector portion 25a using at least one of one combiner and one coupler without using at least one of the two combiners 51 (51a and 51b) and the two couplers 53 (53a and 53b), or without using at least one of a combiner and a coupler.

Next, the configuration of the illumination optical system of the endoscope 11 optically connected to the light source device 12 and the electrical configuration of an imaging system which is connected to the processor 13 will be described.

The illumination optical system of the endoscope 11 includes optical fibers 55a to 55d, fluorescent substances 57 which are arranged at the tip of the optical fibers 55a and 55d, and optical deflection/diffusion members 58 which are arranged at the tip of the optical fibers 55b and 55c.

The optical fibers 55a to 55d constituting the illumination optical system are multi-mode fibers. For example, a thin fiber cable having a core diameter of 105 µm, a cladding diameter of 125 µm, and a diameter including a protective layer as an outer layer of φ0.3 to 0.5 mm can be used.

Narrowband light N1 and N2 from the narrowband light source 41a and 41b of the first illumination light source section 41 are respectively introduced to the optical fibers 55a and 55d extended from the connector portion 25a to the tip portion 35 at an arbitrary timing, and become illumination light through the fluorescent substances 57 serving as wavelength conversion members arranged in the tip portion 35.

Narrowband light N3 to N5 from the narrowband light sources 43a to 43c of the second illumination light source section 43 are respectively introduced to the optical fibers 55b and 55c extended from the connector portion 25a to the tip portion 35, and become illumination light through the optical deflection/diffusion members 58 arranged in the tip portion 35.

The combination of the optical fiber 55a and the fluorescent substance 57 constitutes a projection unit 71a, and the combination of the optical fiber 55b and the optical deflection/diffusion member 58 constitutes a projection unit 71c. The combination of the optical fiber 55c and the optical deflection/diffusion member 58 constitutes a projection unit 71d, and the combination of the optical fiber 55d and the fluorescent substance 57 constitutes a projection unit 71b. A pair of projection units 71a and 71c and a pair of projection units 71b and 71d are arranged on both sides with the imaging element 21 and the objective lens unit 39 of the tip portion 35 of the endoscope 11 sandwiched therebetween.

Figure 4A:
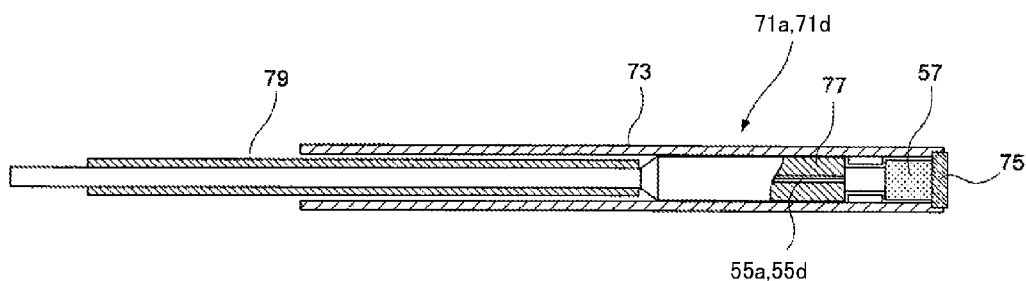
FIGS. 4A and 4B are sectional configuration diagrams of a projection unit including a fluorescent substance of a tip portion of an endoscope in the endoscope apparatus shown in FIG. 1, and a projection unit including an optical deflection/diffusion member.
Figure 4B:
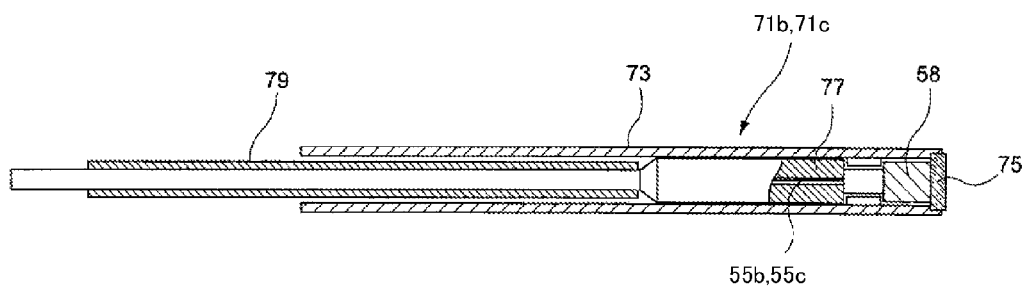

FIG. 4A is a sectional configuration diagram of the projection units 71a and 71d. FIG. 4B is a sectional configuration diagram of the projection units 71b and 71c.

As shown in FIG. 4A, the projection unit 71a and the projection unit 71d have the same configuration, and respectively include a fluorescent substance 57, a cylindrical sleeve member 73 which covers the circumference of the fluorescent substance 57, a protective glass (illumination window) 75 which seals one end of the sleeve member 73, and a ferrule 77 which is inserted into the sleeve member 73 and holds the optical fiber 55a (55d) on the center axis. A flexible sleeve 79 is inserted between the optical fiber 55a (55d) extended from the rear end of the ferrule 77 and the sleeve member 73 so as to cover the outer layer of the optical fiber 55a (55d).

The projection unit 71b and the projection unit 71c have the same configuration, and have the same configuration as the projection units 71a and 71d except that, instead of the fluorescent substances 57 of the projection units 71a and 71d, the optical deflection/diffusion members 58 are arranged, and light is guided from the optical fibers 55b and 55c.

The fluorescent substances 57 of the projection units 71a and 71d include a plurality of fluorescent substance materials (for example, YAG-based fluorescent substances or fluorescent substances, such as BAM (BaMgAl$_{10}$O$_{17}$)) which absorb a part of blue laser light from the narrowband light source 41a, and generate green to yellow excited luminescence light. Thus, green to yellow excited luminescence light excited by blue laser light and blue laser light transmitted by the fluorescent substance 57 without thereby being absorbed are combined to generate white (pseudo white) illumination light.

The fluorescent substance 57 can prevent the occurrence of superimposition of noise causing failure of imaging or flickering at the time of motion image display due to a spectrum caused by coherence of laser light. It is preferable that the fluorescent substance 57 is made of a material, in which a fluorescent material and a filler have a particle size such that a small amount of infrared light is absorbed and a large amount of infrared light is scattered, taking into consideration a difference in the refractive index between a fluorescent material constituting the fluorescent substance and resin for fixation/solidification. Thus, a scattering effect increases without lowering light intensity with respect to red or infrared light, and an optical loss decreases.

Figure 5A:
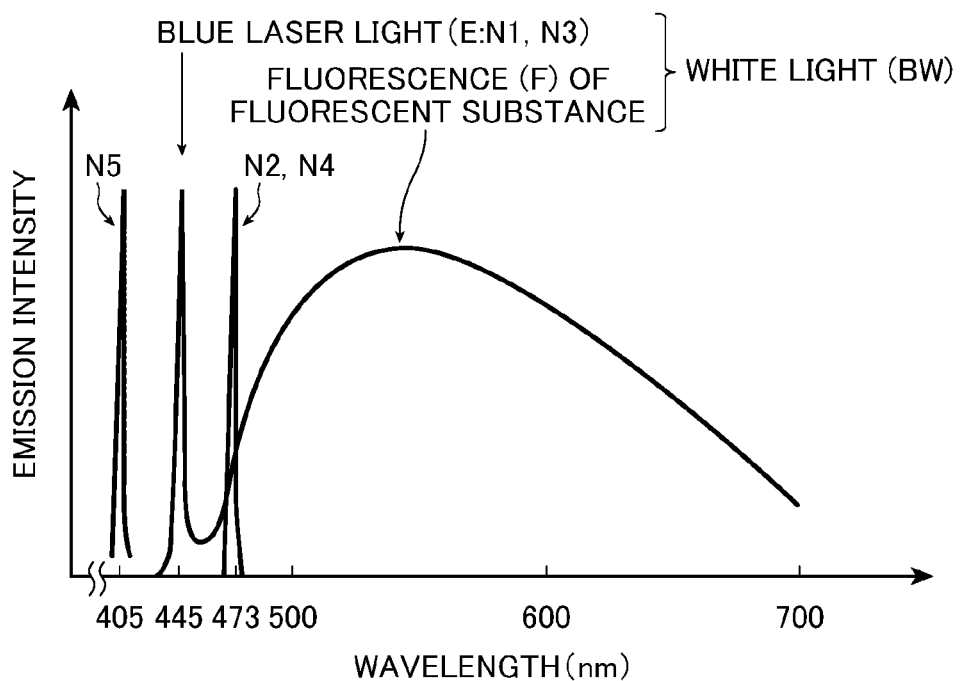
FIG. 5A is a graph showing blue laser light from a narrowband light source for use in the endoscope apparatus shown in FIG. 1, an emission spectrum when blue laser light is wavelength-converted by a fluorescent substance, and an emission spectrum of a laser light from each narrowband light source.

FIG. 5A is a graph showing blue laser light (excitation light E:narrowband light N1) from the narrowband light source 41a, an emission spectrum (fluorescence) F when blue laser light E is wavelength-converted by the fluorescent substance 57, and the emission spectrum of laser light (narrowband light N2 and N5) from the narrowband light source 41b and the narrowband light source 43c. The emission spectrum of laser light (narrowband light N3 and N4) from the narrowband light sources 43a and 43b is the same as the emission spectrum of laser light (excitation light E (N1) and narrowband light N2) from the narrowband light sources 41a and 41b.

Blue laser light E from the narrowband light sources 41a and 43a is expressed by an emission line having a center wavelength of 445 nm, and fluorescence (excited luminescence light) F from the fluorescent substance 57 due to blue laser light E from the narrowband light source 41a has a spectral intensity distribution in which emission intensity increases in a wavelength band of about 450 nm to 700 nm. The above-described pseudo white light BW is formed by a profile based on fluorescence F and blue laser light E. As in this configuration example, if a semiconductor light-emitting element is used as an excitation light source, high-intensity white light is obtained with high emission efficiency, making it possible to easily adjust the intensity of white light and to suppress changes in the color temperature and chromaticity of white light to be small.

White light used herein is not strictly limited to include all wavelength components of visible light. For example, white light may include light in a specific wavelength band of R (red), G (green), or B (blue) which are standard colors. For example, white light broadly includes light including wavelength components from green to red, light including wavelength components from blue to green, or the like.

Broadband light used herein preferably includes at least light regarded as white light, and may include light in at least one of the near-infrared or infrared wavelength band and the near-ultraviolet or ultraviolet wavelength band.

Meanwhile, narrowband light used herein preferably refers to light which belongs to one of the specific wavelength bands of the standard colors R, G, B, and the like, light having a wavelength band separated from a wavelength band of another narrowband light, or light having a wavelength bandwidth of 20 nm, preferably, ±10 nm with respect to the center wavelength.

Blue-green laser light N2 and N4 from the narrowband light sources 41b and 43b are expressed by an emission line having a center wavelength of 473 nm, and blue-violet laser light from the narrowband light source 43c is expressed by an emission line having a center wavelength of 405 nm.

Blue-green laser light N2 from the narrowband light source 41b of the first illumination light source section 41 is also irradiated onto the fluorescent substance 57. For this reason, blue-green laser light N2 has a function of exciting the fluorescent substance 57. However, this function is extremely or significantly weak compared to blue laser light, and most of blue-green laser light N2 transmits the fluorescent substance 57.

From above, in this embodiment, a laser light source (LD445) which emits blue laser light having a center wavelength of 445 nm can be used as the narrowband light sources 41a and 43a, a laser light source (LD473) which emits a blue laser light having a center wavelength of 473 nm can be used as the narrowband light sources 41b and 43b, and a laser light source (LD405) which emits blue laser light having a center wavelength of 405 nm can be used as the narrowband light source 43c.

The optical deflection/diffusion members 58 of the projection units 71b and 71c may be made of a material which transmits blue laser light N3, blue-green laser light N4, and blue-violet laser light N5 from the narrowband light sources 43a to 43c. For example, a resin material, glass, or the like having translucency is used. The optical deflection/diffusion member 58 may have a configuration in which an optical diffusion layer with minute concavo-convexes or in which particles (filler or the like) having different reflective indexes are mixed, on the surface of a resin material, glass, or the like is provided or a configuration in which a semitransparent material is used. Thus, transmitted light emitted from the optical deflection/diffusion member 58 becomes illumination light having a narrowband wavelength whose light quantity is uniformized in a predetermined irradiation region.

Next, as shown in FIG. 2, the imaging system of the endoscope 11 has an imaging control section 62 which supplies a driving signal to the imaging element 21 on the basis of an instruction according to each observation mode from the control section 65, which issues an instruction to the light source control section 49 of the light source device 12 in accordance with each observation mode, an imaging element 21 which images a region to be observed of the subject on the basis of the driving signal from the imaging control section 62 at a predetermined frame rate according to each observation mode, acquires image information, and outputs the image signal of the acquired captured image, and an analog processing circuit (AFE (Analog Front End)) 61 which processes an analog image from the imaging element 21 to a digital signal so as to be processed by a digital signal process in a digital signal processing section 64 of the processor 13.

The imaging control section 62 controls the driving of the imaging element 21 on the basis of an instruction according to each observation mode from the control section 65. Specifically, the imaging control section 62 controls imaging by the imaging element 21 and the output of a captured image signal from the imaging element 21 in each imaging frame in accordance with the emission of the narrowband light source 41a to 41b of the first illumination light source section 41 and the narrowband light sources 43a to 43c of the second illumination light source section 43 in the light source device 12 which is controlled in accordance with the observation mode.

The imaging control of the imaging element 21 by the imaging control section 62, that is, imaging frame control will be described below in detail.

Figure 5B:
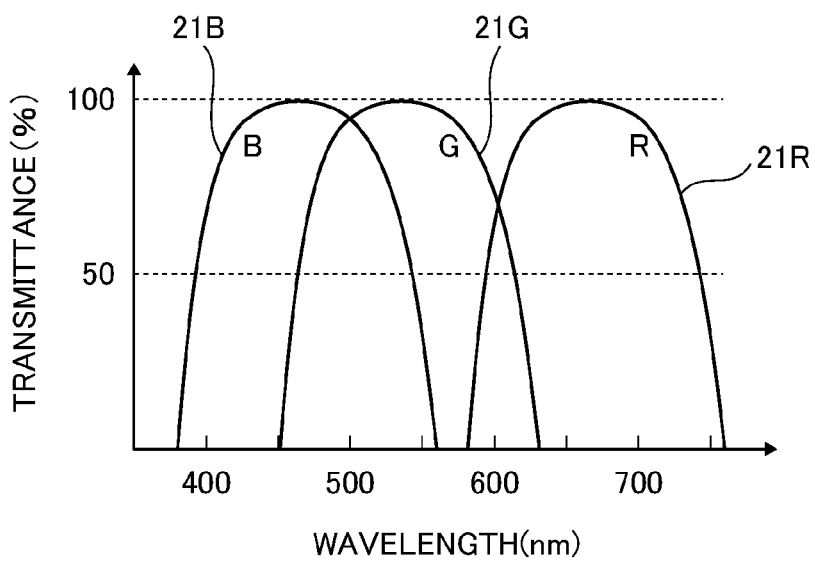
FIG. 5B is a graph showing spectral transmittance of a color filter of an imaging element for use in the endoscope apparatus shown in FIG. 1.

The imaging element 21 is constituted by a color image sensor, such as a CCD (Charge Coupled Device) image sensor or a CMOS (Complementary Metal-Oxide Semiconductor) image sensor, which receives return light from the region to be observed and acquires captured image information. The imaging element 21 is controlled in accordance with each observation mode by the imaging control section 62, and forms the shape of the region to be observed of the subject, onto which the illumination light of the light source device 12 is irradiated, on the light-receiving surface of the imaging element 21 by the objective lens unit 39 to capture an image in each frame. In this embodiment, the imaging element 21 is a color CCD image sensor, and on the light-receiving surface of the imaging element 21, for example, color filters 21R, 21G, and 21B of R, G, and B colors having spectral transmittance shown in FIG. 5B are provided. Three pixels of an R pixel, a G pixel, and a B pixel constitute one set, and a plurality of sets of pixels are arranged in a matrix.

Illumination light including pseudo white light produced by blue laser light (excitation light) from narrowband light source 41a of the first illumination light source section 41 of the light source device 12 and fluorescence (excited luminescence light) from the fluorescent substance 57, and narrowband light N2 to N5 which are laser light from the narrowband light sources 41b and 43a to 43c, is controlled by the light source control section 49 in accordance with each observation mode, and irradiated from the tip portion 35 of the endoscope 11 toward the region to be observed of the subject.

Thus, imaging element 21 images the region to be observed, onto which illumination light from the light source device 12 controlled by the light source control section 49 in accordance with each observation mode is irradiated, in each frame according to each observation mode controlled by the imaging control section 62. As a result, the imaging element 21 is controlled by an imaging control signal according to each observation mode transmitted from the imaging control section 62 through a scope cable 59, and outputs an image signal of a captured image at a predetermined frame rate.

The image signal of the captured image output from the imaging element 21 is transmitted to the analog processing circuit (AFE) 61 through the scope cable 59, subjected to various analog signal processes, converted to a digital signal, and input to the processor 13 through the connector portion 25b.

The AFE 61 converts the image obtained by the imaging element 21 in a digital format while suppressing various kinds of noise at the time of analog-to-digital conversion (A/D) to be the minimum so as to transmit the image to a digital back end, such as the DSP 64, as faithfully as possible.

Though not shown, the AFE 61 includes, for example, a correlated double sampling circuit (CDS), an automatic gain control circuit (AGC), and an analog/digital (A/D) converter. The CDS performs a correlated double sampling process on the captured image signal from the imaging element (CCD) 21, and eliminates noise due to the driving of the imaging element 21. The AGC amplifies the captured image signal with noise removed by the CDS. The A/D converter converts the captured image signal amplified by the AGC to a digital captured image signal having a predetermined number of bits and inputs the result to the processor 13.

In the processor 13, various processes are performed on a digital image signal in accordance with each observation mode, and image information including biological information, such as blood vessel image information of the region to be observed of the subject, is generated and displayed on the display section 15 as an endoscope diagnosis/observation image.

The details of the processor 13 will be described below.

Next, the configuration of the tip portion of the endoscope will be described in detail.

Figure 6:
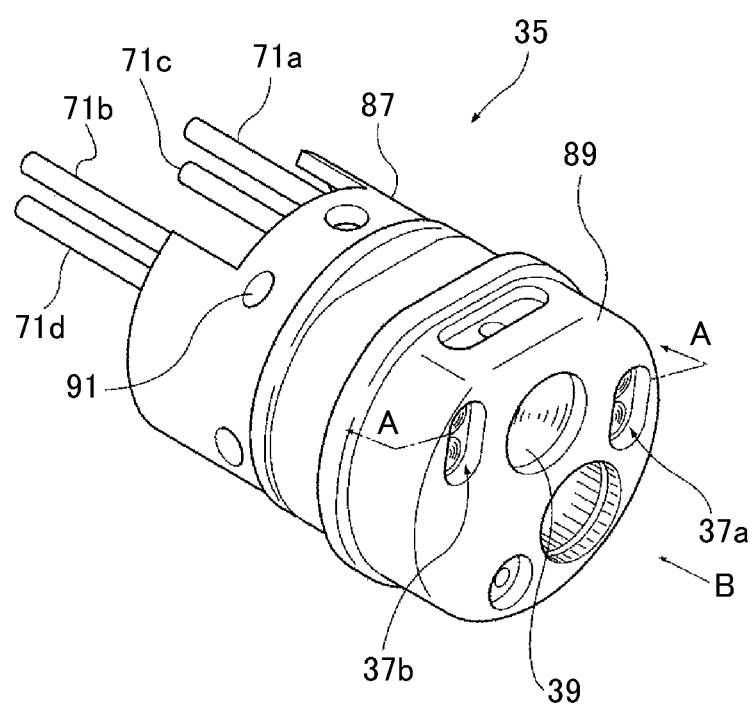
FIG. 6 is a perspective view showing the schematic configuration of an example of a tip portion of an endoscope in the endoscope apparatus shown in FIG. 1.
Figure 7:
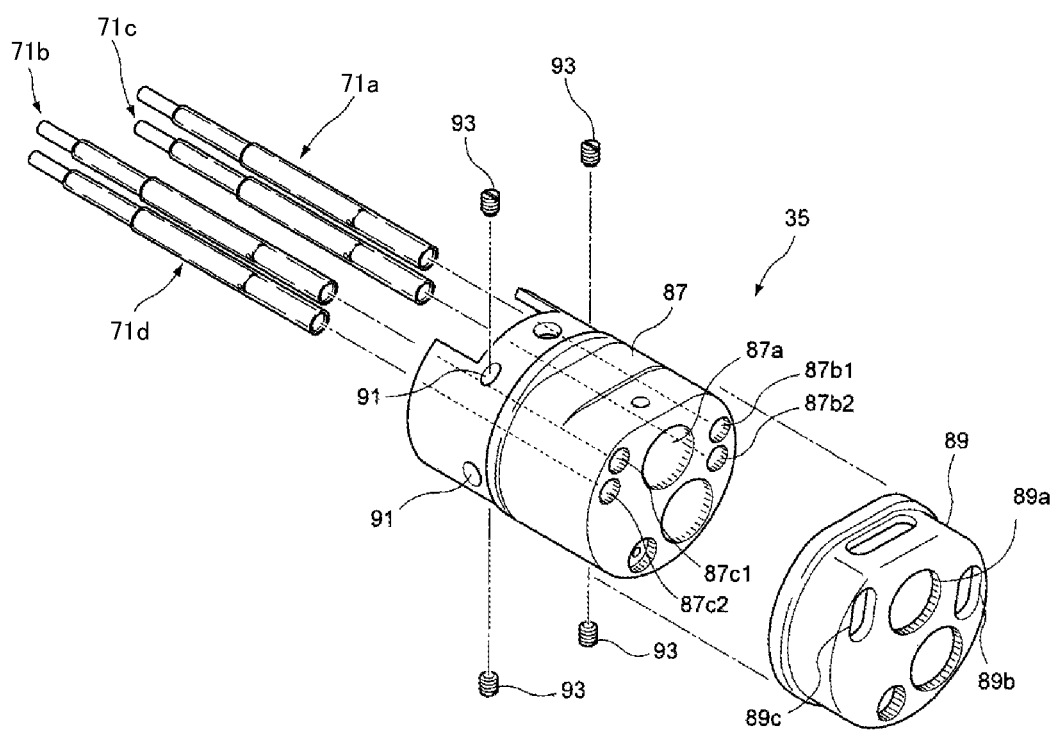
FIG. 7 is an exploded view of the tip portion of the endoscope shown in FIG. 6.

FIG. 6 is a perspective view showing the schematic configuration of the tip portion of the endoscope. FIG. 7 is an exploded view of the tip portion of the endoscope shown in FIG. 6.

As shown in FIGS. 5 and 6, the tip portion 35 of the endoscope 11 is configured such that various components, such as the projection units 71a to 71d, are attached to a hard tip portion 87 which is formed of stainless steel or the like to have a plurality of bores along the longitudinal direction. The hard tip portion 87 has a bore 87a in which the imaging optical system including the imaging element 21 shown in FIG. 2 is accommodated, and bores 87b1, 87b2, 87c1, and 87c2 are formed on both sides of the bore 87a. The projection units 71a and 71c are inserted into the bores 87b1 and 87b2, and the projection units 71b and 71d are inserted into the bores 87c1 and 87c2.

The tip of the hard tip portion 87 is covered by a rubber tip cap 89, and the circumference of the hard tip portion 87 is covered by an outer sheath tube (not shown). Bores 89a, 89b, 89c, ... corresponding to the bores 87a, 87b1, 87b2, 87c1, 87c2, ... of the hard tip portion 87 are formed in the rubber tip cap 89 to open the observation window 40 by the objective lens unit 39 or the irradiation openings 37a and 37b of the projection units 71a to 71d.

Figure 8:
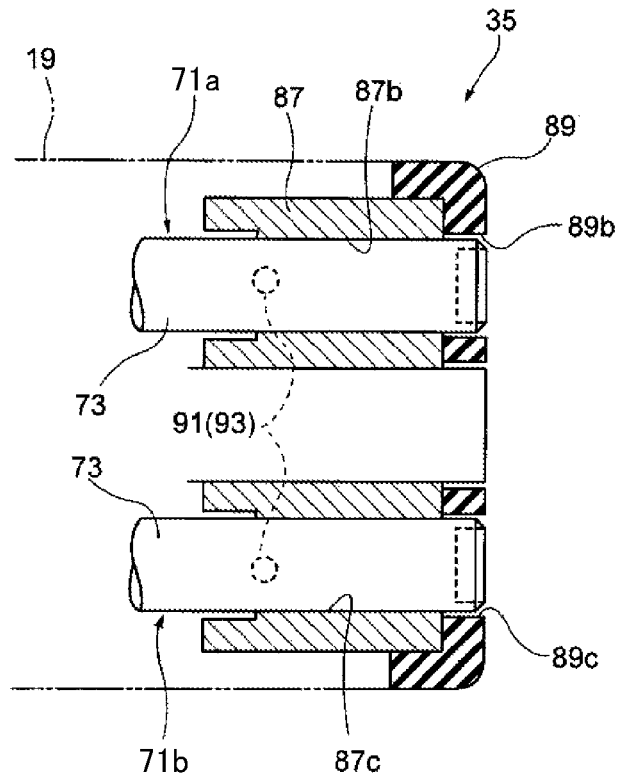
FIG. 8 is a sectional view taken along the line A-A of FIG. 6.

FIG. 8 is a sectional view taken along the line A-A of FIG. 6. The projection units 71a and 71b are inserted into the bores 87b1 and 87c1 of the hard tip portion 87 and then fastened with set screws 93 from a pair of horizontal holes 91 (see FIGS. 6 and 7) communicating with the bores 87b1 and 87c1, such that the projection units 71a and 71b are fixed to the hard tip portion 87. Similarly, the projection units 71c and 71d are fastened with set screws 93 and fixed to the hard tip portion 87.

According to the configuration of the endoscope including the projection units 71a to 71d, the projection units 71a to 71d are detachably fixed by the set screws 93 in a state of being inserted into the bores 87b1, 87b2, 87c1, and 87c2 of the hard tip portion 87. For this reason, the replacement of the projection units 71a to 71d is easily done, thereby improving the maintenance of the endoscope. That is, when attenuation of illumination light intensity or changes in color occur due to the long-term use of the endoscope, replacement with a new projection unit is simply done.

Next, illumination patterns through which laser light from the laser light sources LD1 to LD5 are appropriately combined and emitted by the projection units 71a to 71d to generate various kinds of illumination light will be described.

Figure 9:
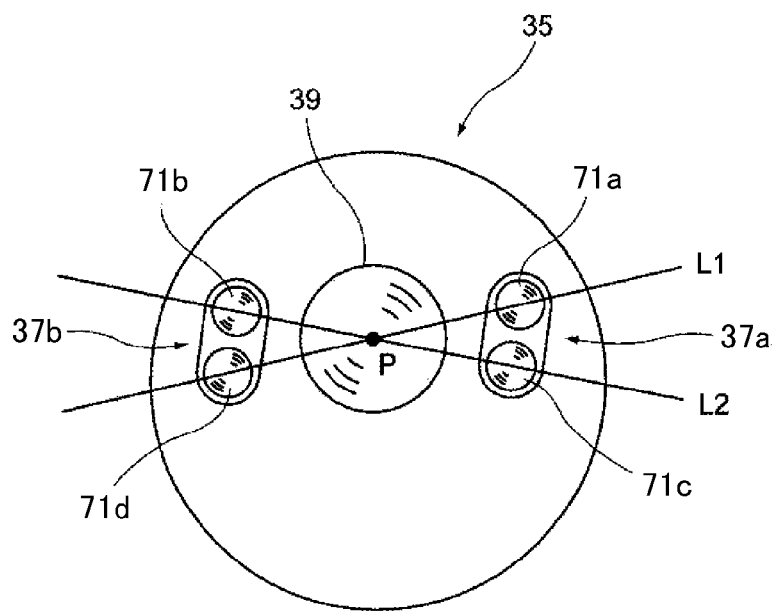
FIG. 9 is a front view of the tip portion of the endoscope shown in FIG. 6 when viewed from a B direction.

FIG. 9 is a front view of the tip portion of the endoscope 11 shown in FIG. 6 when viewed from a B direction. As described above, the projection units 71a to 71d are arranged on both sides of the objective lens unit 39 such that the projection units 71a and 71c perform irradiation from the irradiation opening 37a, and the projection units 71b and 71d perform irradiation from the irradiation opening 37b. A pair of projection units 71a and 71d including the fluorescent substances (see FIG. 4A) are arranged such that a line L1 connecting the positions of the protective glasses 75 (see FIG. 4) serving as an illumination window cuts across the region of the objective lens unit 39 serving as the observation window 40. A pair of projection units 71b and 71c including the optical deflection/diffusion members 58 (see FIG. 4B) are arranged such that a line L2 connecting the positions of the protective glasses 75 (see FIG. 4) cuts across the region of the objective lens unit 39.

The projection units 71a to 71d are arranged in the increased space efficiency such that the lines L1 and L2 have a cross point P in the region of the objective lens unit 39. That is, the projection units 71a and 71d which irradiate white illumination light are arranged at the positions with the objective lens unit 39 of the tip portion 35 sandwiched therebetween, and irradiate white light from both sides of the objective lens unit 39, thereby preventing the occurrence of illumination irregularity.

Although in the example of the drawing, a four-light type is provided in which the four projection units 71a to 71d, including the two projection units 71a and 71b with the fluorescent substances 57, are arranged in the tip portion 35 of the endoscope 11 at the positions with the objective lens unit 39 for the imaging element 21, the invention is not limited thereto. If one projection unit includes the fluorescent substance 57, a two-light type may be provided in which the two projection units 71a and 71c or 71b and 71d, preferably, the two projection units 71a and 71d or 71b and 71c are arranged in the tip portion 35 of the endoscope 11 at the positions with the objective lens unit 39 for the imaging element 21 sandwiched therebetween.

Next, the processor 13 will be described in detail with reference to FIGS. 2 and 3.

As shown in FIGS. 2 and 3, the processor 13 has a digital signal processing section (DSP (Digital Signal Processor)) 64 which performs a digital signal process on the digital image signal of each observation mode transmitted from the endoscope 11, an image processing section 63 which performs an image process according to each observation mode on image data subjected to the digital signal process of each observation mode, a control section 65 which performs display control for displaying an observation image based on image data subjected to image process on the display section 15 or controls the respective sections of the endoscope 11, the light source device 12, and the processor 13, and a storage section 67 which stores the image data signal of the captured image of each observation mode.

The DSP 64 receives the digital image signal of the captured image of each observation mode captured by the imaging element 21 and transmitted from the AFE 61 of the imaging system of the endoscope 11 through the connector portion 25b, and performs various processes, such as color separation, color interpolation, color correction, white balance adjustment, gamma correction, and contour enhancement, on the received digital image signal to generate captured image data of each observation mode subjected to the digital signal process. Image data of the captured image of each observation mode generated by the DSP 64 is transmitted to the image processing section 63 and, if necessary, is stored in the storage section 67.

As shown in FIG. 3, the image processing section 63 performs an image process according to each observation mode on image data of the captured image of each observation mode subjected to the digital signal process in the DSP 64. The image processing section 63 has a normal light image processing section 102 which performs an image process on the captured image using broadband light (white light) in the normal observation mode, and a special light image processing section 104 which performs an image process on the captured image using broadband light and narrowband light in the special light observation mode. Image data of the captured image of each observation mode subjected to the image process in the image processing section 63 is transmitted to the control section 65 and, if necessary, is stored in the storage section 67.

In the normal observation mode, the normal light image processing section 102 performs a predetermined image process suitable for a normal observation image by white light from the narrowband light source 41a of the first illumination light source section 41 of the light source device 12 and the fluorescent substance 57 on image data of the captured data transmitted from the DSP 64 or read from the storage section 67, outputs normal light image data, stores normal light image data in the storage section 67, and causes the display section 15 to display a normal observation image by white light.

In the special light observation mode using narrowband light, the special light image processing section 104 performs a predetermined image process suitable for a special light observation image by narrowband light on image data of the captured image transmitted from the DSP 64 or read from the storage section 67, and outputs special light image data. The special light image processing section 104 has a first image processing section 106 which performs an image process on a captured image by white light and narrowband light N2 from the narrowband light source 41b of the first illumination light source section 41 in the screening diagnosis mode of the special light observation mode, and a second image processing section 108 which performs an image process on a captured image by white light and narrowband light N3, N4, and N5 from the narrowband light sources 43a to 43c of the second illumination light source section 43 in the detailed diagnosis mode of the special light observation mode.

In the embodiment of the drawing, the special light image processing section 104 performs an image process for calculating oxygen saturation as the blood vessel image information of the region to be observed of the subject to generate an oxygen saturation image. Thus, the first image processing section 106 and the second image processing section 108 also generate an oxygen saturation image.

Hereinafter, the control of the light source device 12 in the screening diagnosis mode and the detailed diagnosis mode of the special light observation mode in the endoscope apparatus of the invention, and the first image processing section and the second image processing section of the special light image processing section of the image processing section of the processor will be described.

Figure 10:
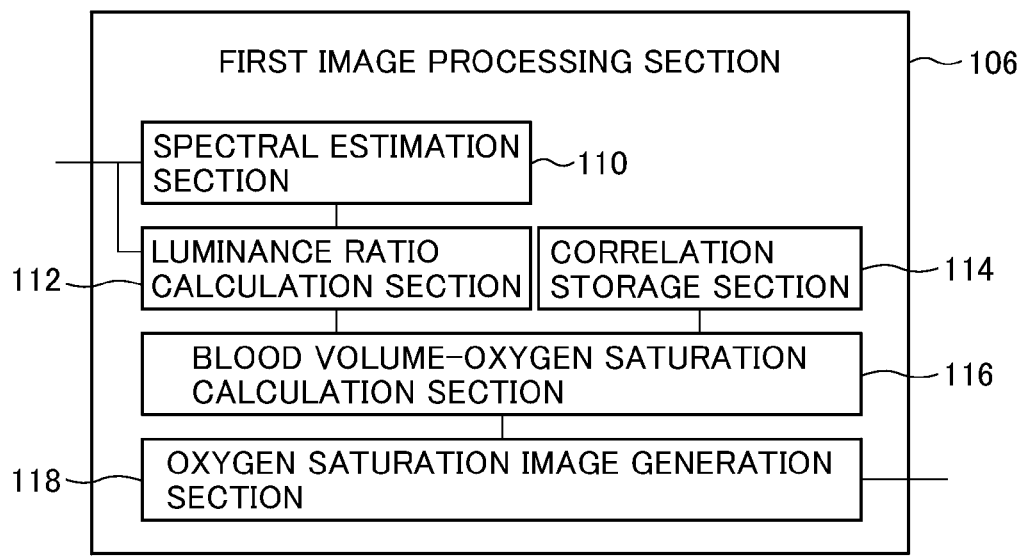
FIG. 10 is a block diagram showing the configuration of an example of a first image processing section of a special light image processing section of an image processing section in the endoscope apparatus shown in FIG. 3.
Figure 12:
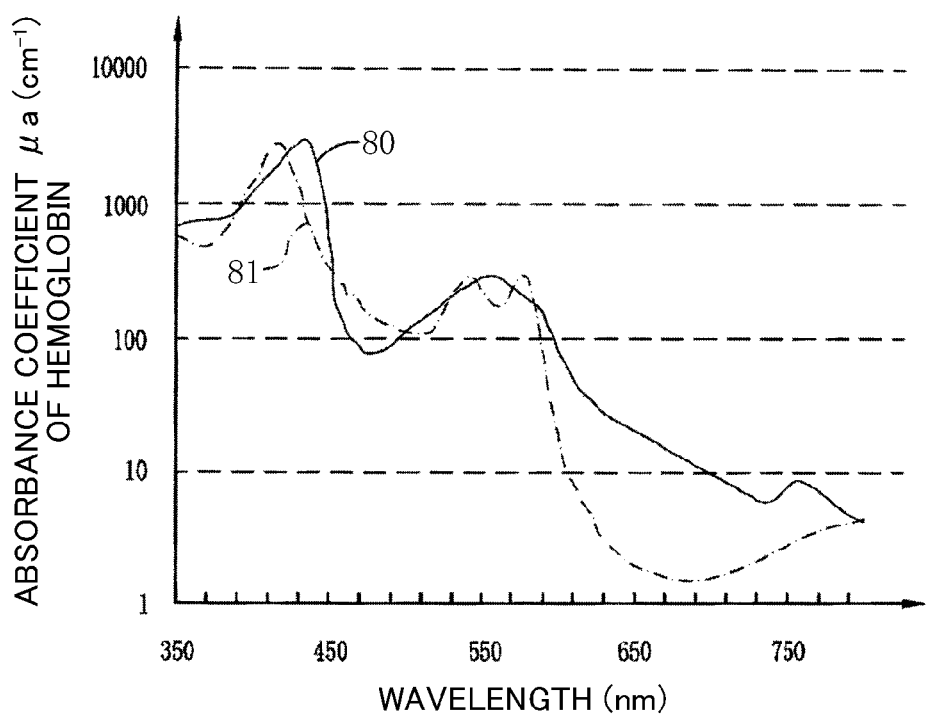
FIG. 12 is a graph showing the wavelength dependency of an absorption coefficient of hemoglobin in a blood vessel.
Figure 11:
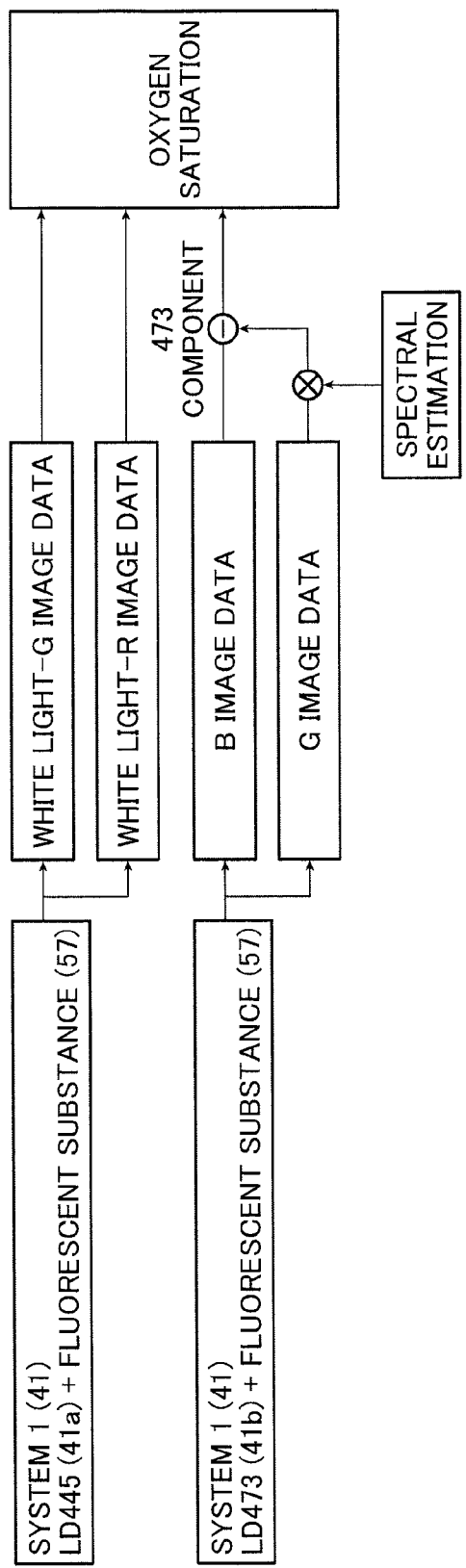
FIG. 11 is an explanatory view illustrating a process for calculating oxygen saturation in a screening diagnosis mode of the endoscope apparatus shown in FIG. 1.
Figure 13:
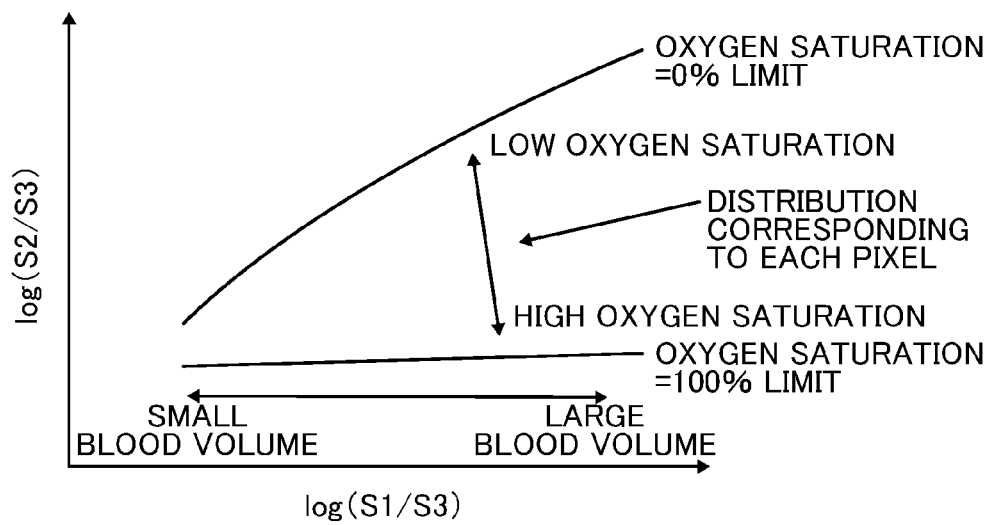
FIG. 13 is a graph showing the correlation between the spectral luminance ratio of the pixel of a captured image, blood volume, and oxygen saturation.
Figure 14:
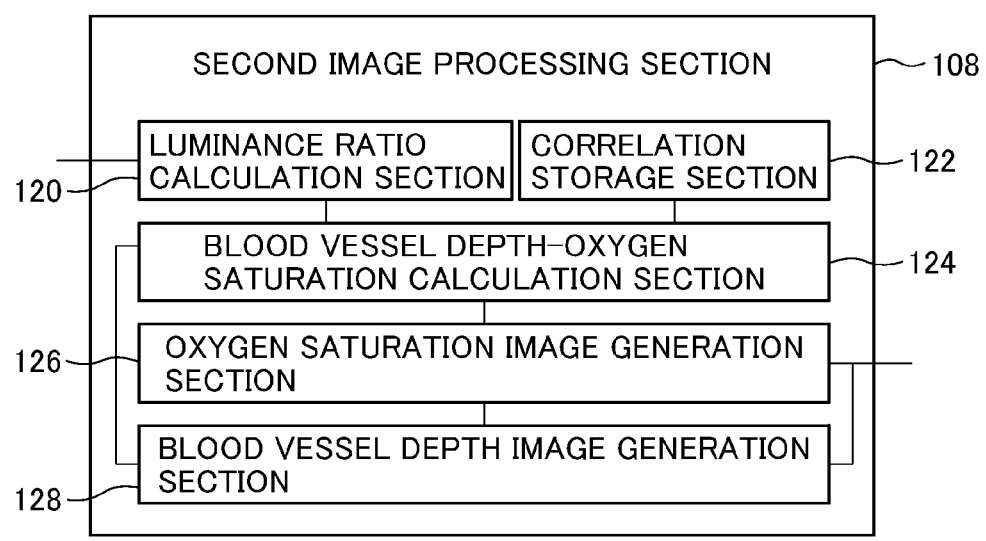
FIG. 14 is a block diagram showing the configuration of an example of a second image processing section of a special light image processing section of an image processing section in the endoscope apparatus shown in FIG. 3.
Figure 15:
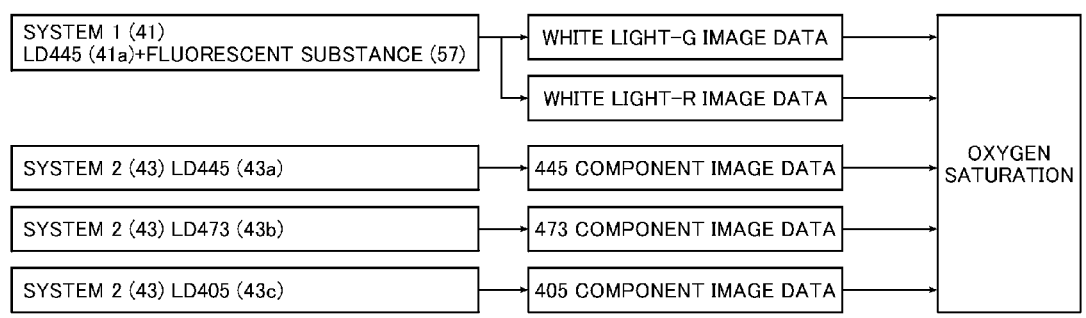
FIG. 15 is an explanatory view illustrating a process for calculating oxygen saturation in a detailed diagnosis mode of the endoscope apparatus shown in FIG. 1.
Figure 16:
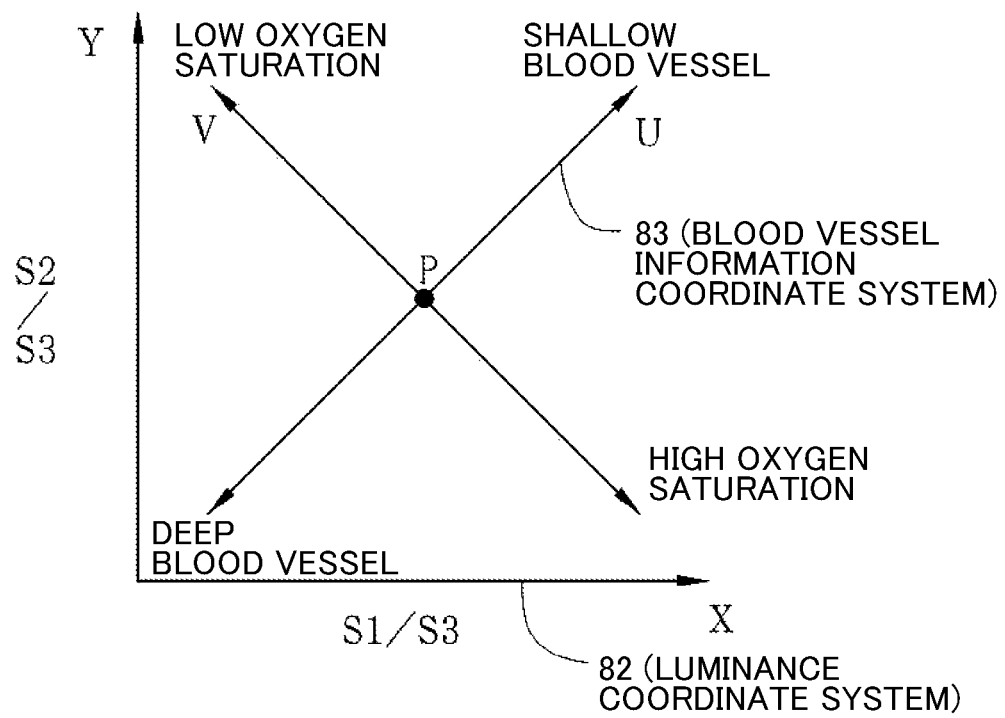
FIG. 16 is a graph showing the correlation between the spectral luminance ratio of pixels of a captured image, a blood vessel depth, and oxygen saturation.

FIG. 10 is a block diagram showing the configuration of an example of the first image processing section of the special light image processing section of the image processing section shown in FIG. 3. FIG. 11 is an explanatory view illustrating a process for calculating oxygen saturation in the screening diagnosis mode. FIG. 12 is a graph showing the wavelength dependency of an absorption coefficient of hemoglobin in a blood vessel. FIG. 13 is a graph showing the correlation between the spectral luminance ratio (S1/S3, S2/S3) of pixels of a captured image, blood volume, and oxygen saturation. FIG. 14 is a block diagram showing the configuration of an example of the second image processing section of the special light image processing section of the image processing section in the endoscope apparatus shown in FIG. 3. FIG. 15 is an explanatory view illustrating a process for calculating oxygen saturation in the detailed diagnosis mode of the endoscope apparatus shown in FIG. 1. FIG. 16 is a graph showing the correlation between the spectral luminance ratio (S1/S3, S2/S3) of pixels of a captured image, blood vessel depth, and oxygen saturation.

As shown in FIG. 10, in the screening diagnosis mode, the first image processing section 106 calculates information on the oxygen saturation of hemoglobin in the blood of the subject on the basis of captured image data by narrowband light N2 in which pseudo white light from the narrowband light source 41a and the fluorescent substance 57 of the first illumination light source section 41 and fluorescence from the narrowband light source 41b and the fluorescent substance 57 are mixed, and outputs an oxygen saturation image for pseudo-color displaying the distribution of oxygen saturation on the basis of the information on the calculated oxygen saturation. The first image processing section 106 has a spectral estimation section 110, a luminance ratio calculation section 112, a correlation storage section 114, a blood volume-oxygen saturation calculation section 116, and an oxygen saturation image generation section 118.

In the screening diagnosis mode, as shown in FIG. 11 and Table 1, the first illumination light source section 41 of the system 1 is used. In the first frame, captured image data (white light RGB image data) by pseudo white light from the combination of the narrowband light source 41a (LD445) turned on by the light source control section 49 and the fluorescent substance 57 is acquired by the imaging element 21 which is controlled by the imaging control section 62, and a normal observation image is generated. In the second frame, captured image data (RGB image data) by the combination of narrowband light N2 and fluorescence from the combination of the narrowband light source 41b (LD473) turned on by the light source control section 49 and the fluorescent substance 57 is acquired by the imaging element 21 which is controlled by the imaging control section 62, and an oxygen saturation image is generated. That is, the narrowband light sources 41a and 41b are repeatedly alternately turned on/off in each frame.

TABLE 1

| Diagnosis Mode | Frame 1 | Frame 2 | Frame 3 | Frame 4 |
|---|---|---|---|---|
| Screening Diagnosis Mode | System 1-LD445 | System 2-LD473 | — | — |
| Detailed Diagnosis Mode | System 1-LD445 | System 2-LD445 | System 2-LD473 | System 2-LD405 |

White light B image data, white light G image data, and white light R image data acquired in the first frame are obtained by the imaging element 21 having the above-described color filters (B filter 21B, G filter 21G, and R filter 21R) shown in FIG. 5B from the whole B wavelength region, the whole G wavelength region, and the R wavelength region of return light of irradiated white light. In the first frame, the normal light image processing section 102 generates normal light image data of a normal observation image by white light on the basis of acquired white light BGR image data, and stores normal light image data in the storage section 67. It is preferable that white light RGB image data acquired in the first frame is stored in the storage section 67.

B image data and R image data acquired in the second frame include a small amount of fluorescence in the G to R wavelength regions emitted from the fluorescent substance 57 even though narrowband light N2 (473 nm) is dominant. For this reason, B image data and R image data do not represent spectral image data (hereinafter, referred to as 473 component image data) of only the narrowband light N2 (473 nm) component. It is preferable that RGB image data acquired in the second frame is stored in the storage section 67.

For this reason, in the screening diagnosis mode, the spectral estimation section 110 reads RGB image data acquired in the second frame from the storage section 67, and obtains 473 component image data by spectral estimation from read RGB image data. That is, as shown in FIG. 11, in the second frame, the spectral estimation section 110 performs spectral estimation from captured image data (RGB image data) acquired from the combination of narrowband light N2 and fluorescence emitted from the combination of the narrowband light source 41b (LD473) and the fluorescent substance 57 to calculate a G fluorescent component in G image data, from the calculated G fluorescent component and the fluorescent characteristic of the fluorescent substance 57 when a predetermined amount of narrowband light N2 is used as excitation light, that is, multiplies the ratio of the G fluorescent component to the fluorescent characteristic of the fluorescent substance 57 to calculate a B fluorescent component in B image data with respect to the calculated G fluorescent component, and subtracts the calculated B fluorescent component from B image data to obtain 473 component image data.

The spectral estimation method which obtains 473 component image data from RGB image data is not particularly limited, and a known spectral estimation method in the related art may be used. For example, a spectral estimation method described in JP 2003-93336 A which obtains spectral images may be used.

The luminance ratio calculation section 112 specifies a blood vessel region including the blood vessel from white light G image data and white light R image data of the first frame read from the storage section 67, and 473 component image data calculated by the spectral estimation section 110 from the B image data and R image data calculated in the second frame. When the luminance values of the pixels of image data corresponding to reflected light of two kinds of illumination light in a wavelength range in which, with regard to the pixels at the same pixels in the blood vessel region, the magnitude relationship between the absorbance coefficients (absorbance) (see FIG. 12) of reduced hemoglobin and oxidized hemoglobin is reversed in accordance with the oxygen saturation of hemoglobin in the blood are S1 and S2, and the luminance value of the pixel of image data corresponding to reflected light of one kind of illumination light in a wavelength range in which the absorbance coefficients become equal is S3, the luminance ratio calculation section 112 obtains first and second luminance ratios S1/S3 and S2/S3. S1 represents the luminance value of the pixel of white light R image data, S2 represents the luminance value of the pixel of 473 component image data, and S3 represents the luminance value of the pixel of white light G image data. As the method of specifying a blood vessel, for example, a method may be used in which a blood vessel region is obtained from a difference between the luminance value of the blood vessel portion and the luminance value of another portion.

The correlation storage section 114 stores the correlation between the first and second luminance ratios S1/S3 and S2/S3, blood volume, and oxygen saturation. This correlation is a correlation when the blood vessel has the absorbance coefficient of hemoglobin shown in FIG. 12, and is obtained by analyzing multiple image data accumulated by previous diagnosis or the like.

As shown in FIG. 12, hemoglobin in the blood has an absorbance characteristic such that an absorbance coefficient $\mu a$ changes depending on the wavelength of light to be irradiated. The absorbance coefficient $\mu a$ indicates an absorbance which is the magnitude of light absorption of hemoglobin. For example, the absorbance coefficient $\mu a$ is a coefficient of Expression $I0\exp(-\mu a \times x)$ which represents the attenuation situation of light irradiated onto hemoglobin. I0 is the intensity of light irradiated onto the subject tissue from the light source device, and x (cm) is the depth to the blood vessel in the subject tissue.

As shown in FIG. 12, reduced hemoglobin 80 which is not bound to oxygen and oxidized hemoglobin 81 which is bound to oxygen have different absorbance characteristics, and there is a difference in the absorbance excluding an isosbestic point (in FIG. 12, a cross point of hemoglobin 80 and 81) representing the same absorbance (absorbance coefficient $\mu a$). If there is a difference in the absorbance, even when light having the same intensity and wavelength is irradiated onto the same blood vessel, the luminance value changes. Even when light having the same intensity is irradiated, if light is different in wavelength, the absorbance coefficient $\mu a$ changes, causing a change in the luminance value.

In general, since the distribution of FIG. 12 changes non-linearly depending on an imaging-target site, it is necessary to obtain the distribution in advance by actual biological tissue measurement, light propagation simulation, or the like.

FIG. 13 is a graph showing the correlation between the first and second luminance ratios S1/S3 and S2/S3, blood volume, and oxygen saturation. In the graph, the horizontal axis is log(S1/S3), and the vertical log(S2/S3). The first luminance ratio S1/S3 corresponds to white light R image data/white light G image data, and the second luminance ratio S2/S3 corresponds to 473 component image data/white light G image data. As shown in the graph, the value of the first luminance ratio S1/S3 changes depending on the blood volume and increases as the blood volume increases. The value of the second luminance ratio S2/S3 changes depending on both the blood volume and the oxygen saturation. That is, the value of the second luminance ratio S2/S3 increases as the blood volume increases or as the oxygen saturation is lowered.

The calculation of blood volume and oxygen saturation using the luminance values S1, S2, and S3 will be described.

In general, if light enters the mucosal tissue of the subject, a part of light is absorbed in the blood vessel, and another part of light having not been absorbed returns as reflected light. At this time, the deeper the blood vessel is, the larger the influence of scattering from overlying tissue becomes.

On the other hand, light in a wavelength range of 470 to 700 nm has features that the scattering coefficient in the mucosal tissue is small, and the wavelength dependency is small. For this reason, with the use of light in this wavelength range as illumination light, it is possible to obtain blood information including information regarding the blood volume and the oxygen saturation without reducing an influence of the depth of the blood vessel. Thus, in the endoscope apparatus 10, the oxygen saturation of hemoglobin in the blood is calculated using image signals corresponding to reflected light in three or more different wavelength ranges of 460 to 700 nm including reflected light in two or more wavelength ranges in which the absorbance coefficient changes depending on the oxygen saturation of hemoglobin in the blood and one or more wavelength ranges in which the absorbance coefficient is not changed.

The following three features can be thought from the wavelength dependency of the absorbance coefficient of hemoglobin in the blood shown in FIG. 12.

The absorbance coefficient significantly changes depending on changes in the oxygen saturation in the vicinity of the wavelength 470 nm (for example, a B wavelength range of the center wavelength 470 nm±10 nm), and the absorbance coefficient of oxidized hemoglobin 81 is larger than the absorbance coefficient of reduced hemoglobin 80.

When averaging in the G wavelength range of 540 to 580 nm, there is little influence of the oxygen saturation. That is, a difference between the absorbance coefficient of oxidized hemoglobin 81 and the absorbance coefficient of reduced hemoglobin 80 is regarded to be small.

In the R wavelength range of 590 to 700 nm, the absorbance coefficient seems to apparently change significantly due to the oxygen saturation, and the absorbance coefficient of reduced hemoglobin 80 is larger than the absorbance coefficient of oxidized hemoglobin 81. However, since the value of the absorbance coefficient is very small in this range, as a result, it can be thought that there is little influence of the oxygen saturation.

There are the following two features from the reflection spectrum of the mucosa.

Although in the R wavelength range, it seems that there is little influence of hemoglobin, absorption occurs in the G wavelength range. For this reason, the larger the blood volume (corresponding to the size of the blood vessel or the density of the blood vessel), the larger the difference between reflectance in the G wavelength range and reflectance in the R wavelength range.

The lower the oxygen saturation or the larger the blood volume, the larger the difference between reflectance in the vicinity of the wavelength 470 nm and reflectance in the G wavelength range.

That is, the value of the second luminance ratio S2/S3 between the luminance value of the pixel of 473 component image data and the luminance value of the pixel of white light G image data changes depending on both the oxygen saturation and the blood volume. The value of the first luminance ratio S1/S3 between the luminance value of the pixel of white light R image data and the luminance value of the pixel of white light G image data changes mainly depending on the blood volume. Thus, with the use of this feature, it is possible to separate the oxygen saturation and the blood volume from the spectral images in the three wavelength ranges including the vicinity of the wavelength 470 nm, and the G and R wavelength ranges, and to accurately calculate the respective values. A graph created on the basis of this feature is the graph of FIG. 13 which shows the correlation between the first and second luminance ratios S1/S3 and S2/S3, blood volume, and oxygen saturation.

The blood volume-oxygen saturation calculation section 116 calculates the blood volume and the oxygen saturation corresponding to the first and second luminance ratios S1/S3 and S2/S3 calculated by the luminance ratio calculation section 112 on the basis of the correlation stored in the correlation storage section 114.

The oxygen saturation image generation section 118 includes a color table (not shown) in which color information is allocated in accordance with the magnitude of the oxygen saturation. In the color table, colors are allocated to be clearly distinguishable in accordance with the degree of the oxygen saturation, for example, cyan at the time of low oxygen saturation, magenta at the time of middle oxygen saturation, and yellow at the time of high oxygen saturation. The oxygen saturation image generation section 118 specifies the color information corresponding to the oxygen saturation calculated by the blood volume-oxygen saturation calculation section 116 using the color table. The color table is switchable in accordance with an instruction input from the input section 17, and is selected in accordance with an observation site, such as stomach, duodenum, or small intestine.

If the color information is specified for all pixels in the blood vessel region, the oxygen saturation image generation section 118 reads normal light image data of a normal observation image by white light which is generated by the normal light image processing section 102 in the first frame and stored in the storage section 67, and reflects and superimposes the color information in and on read normal light image data, that is, synthesizes a color information image with the normal observation image to generate oxygen saturation image data in which the oxygen saturation of hemoglobin in the blood is reflected (pseudo-color display).

Oxygen saturation image data generated by the first image processing section 106 is transmitted to the control section 65, becomes an endoscope observation image together with various kinds of information in the control section 65, and is displayed on the display section 15 as a screening diagnostic image. If necessary, the endoscope observation image is stored in the storage section 67 constituted by a memory or a storage device.

As described above, in the screening diagnosis mode, the normal observation image by white light generated in the first frame and the color information corresponding to the oxygen saturation generated in the second frame can be displayed on the display section 15 in a superimposed manner. That is, the blood vessel image information (biological information) is acquired in the two frames and displayed. For this reason, an image including the displayed blood vessel image information is a smooth image obtained at a high frame rate, and is an image suitable for screening diagnosis.

As shown in FIG. 14, in the detailed diagnosis mode, the second image processing section 108 calculates information on the oxygen saturation of hemoglobin in the blood of the subject on the basis of captured image data by pseudo white light from the narrowband light source 41a of the first illumination light source section 41 and the fluorescent substance 57, and narrowband light N3 to N5 from the narrowband light sources 43a to 43c of the second illumination light source section 43, and outputs an oxygen saturation image for pseudo-color displaying the distribution of the oxygen saturation on the basis of the information of the calculated oxygen saturation. The second image processing section 108 has a luminance ratio calculation section 120, a correlation storage section 122, a blood vessel depth-oxygen saturation calculation section 124, an oxygen saturation image generation section 126, and a blood vessel depth image generation section 128.

In the detailed diagnosis mode, as shown in FIG. 15 and Table 1, both the narrowband light source 41a of the first illumination light source section 41 of the system 1 and the second illumination light source section 43 of the system 2 are used. In the first frame, captured image data (white light RGB image data) by pseudo white light from the combination of the narrowband light source 41a (LD445) and the fluorescent substance 57 is acquired, and a normal observation image is generated. In the second frame, spectral image data (hereinafter, referred to as 445 component image data) of only the narrowband light N3 (445 nm) component from the narrowband light source 43a (LD445) is acquired. In the third frame, 473 component image data which is spectral image data of only the narrowband light N4 (473 nm) component from the narrowband light source 43b (LD445) is acquired. In the fourth frame, spectral image data (hereinafter, referred to as 405 component image data) of only the narrowband light N3 (405 nm) component from the narrowband light source 43c (LD405) is acquired, and an oxygen saturation image is generated.

The light source control section 49 performs turn-on control such that the narrowband light sources 41a and 43a to 43c are turned on only in the first to fourth frames. The imaging control section 62 drives the imaging element 21 in each frame and performs imaging frame control to acquire the respective pieces of image data.

In the first frame of the detailed diagnosis mode, as in the first frame of the screening diagnosis mode, the normal light image processing section 102 generates normal light image data of the normal observation image by white light on the basis of acquired white light BGR image data and stores normal light image data in the storage section 67.

In the second frame, unlike the screening diagnosis mode, only narrowband light N3 having the wavelength of 445 nm is irradiated onto the subject. Thus, even in the imaging element 21 having the color filters shown in FIG. 5B, 445 component image data can be acquired. Similarly, in the third frame, since only narrowband light N4 having the wavelength of 473 nm is irradiated, the imaging element 21 can acquire 473 component image data. In the fourth frame, since only narrowband light N5 having the wavelength of 405 nm is irradiated onto the subject, the imaging element 21 can acquire 405 component image data. It is preferable that 445 component image data, 473 component image data, and 405 component image data acquired in the second to fourth frames are stored in the storage section 67.

The luminance ratio calculation section 120 specifies the blood vessel region including the blood vessel from 445 component image data, 473 component image data, and 405 component image data acquired in the second to fourth frames. When the luminance values of pixels of the image data corresponding to reflected light of two kinds of narrowband light in a wavelength range in which, with regard to the pixels at the same position in the blood vessel, the magnitude relationship between the absorbance coefficients (absorbance) of reduced hemoglobin and oxidized hemoglobin is reversed in accordance with the oxygen saturation of hemoglobin in the blood are S1 and S2, and the luminance value of the pixel of image data corresponding to reflected light of one kind of narrowband light in a wavelength range in which the absorbance coefficients become equal is S3, the luminance ratio calculation section 120 obtains the first and second luminance ratios S1/S3 and S2/S3. S1 represents the luminance value of the pixel of 445 component image data, S2 represents the luminance value of the pixel of 473 component image data, and S3 represents the luminance value of the pixel of 405 component image data.

Taking into consideration the absorbance characteristic of hemoglobin shown in FIG. 12, the wavelengths at which there is the difference in the absorbance due to the oxygen saturation are 445 nm and 405 nm, and a short-wavelength region having a short invasion depth is necessary so as to extract blood vessel depth information. For this reason, it is preferable that the third to fifth narrowband light N3 to N5 include at least one kind of narrowband light having a wavelength region in which the center wavelength is equal to or smaller than 450 nm. In this embodiment such narrowband light corresponds to the third and fifth narrowband light. Even when the oxygen saturation is the same, if the wavelength is different, the value of the absorption coefficient differs, and the invasion depth into the mucosa differs. Therefore, with the use of the characteristic of light whose invasion depth differs depending on the wavelength, it is possible to obtain the correlation between the luminance ratio and the blood vessel depth.

The correlation storage section 122 stores the correlation between the first and second luminance ratios S1/S3 and S2/S3, blood vessel depth, and oxygen saturation. This correlation is also a correlation when the blood vessel has the absorbance coefficient of hemoglobin shown in FIG. 12, and is obtained by analyzing multiple image data accumulated by previous diagnosis or the like.

As shown in FIG. 16, the correlation storage section 122 associates the coordinates of a luminance coordinate system 82 representing the first and second luminance ratios S1/S3 and S2/S3 with the coordinates of a blood vessel information coordinate system 83 representing the oxygen saturation and the blood vessel depth, thereby storing the correlation. The luminance coordinate system 82 is an XY coordinate system in which the X axis represents the first luminance ratio S1/S3 and the Y axis represents the second luminance ratio S2/S3. The blood vessel information coordinate system 83 is the UV coordinate system which is provided on the luminance coordinate system 82 and in which the U axis represents the blood vessel depth and the V axis represents the oxygen saturation. The U axis has a positive slope because the blood vessel depth has a positive correlation with respect to the luminance coordinate system 82. As the position on the U axis moves diagonally upward right, the depth of the blood vessel decreases; as the position on the U axis moves diagonally downward left, the depth of the blood vessel increases. The V axis has a negative slope because the oxygen saturation has a negative correlation with respect to the luminance coordinate system 82. As the position on the V axis moves diagonally upward right, the depth of the oxygen saturation decreases; as the position on the V axis moves diagonally downward left, the oxygen saturation increases.

In the blood vessel information coordinate system 83, the U axis and the V axis are perpendicular to each other at a cross point P. This is because the magnitude relationship of absorbance is reversed between at the time of the irradiation of the third narrowband light N3 of the second frame and at the time of the irradiation of the fourth narrowband light N4 of the third frame. That is, as shown in FIG. 12, when the third narrowband light N3 having a wavelength of 440±10 nm is irradiated, the absorbance coefficient of reduced hemoglobin 80 becomes larger than the absorbance coefficient of oxidized hemoglobin 81 having high oxygen saturation. In contrast, when the fourth narrowband light N4 having a wavelength of 470±10 nm is irradiated, the absorbance coefficient of oxidized hemoglobin 81 becomes larger than the absorbance coefficient of reduced hemoglobin 80, such that the magnitude relationship of absorbance is reversed.

When, instead of the third to fifth narrowband light N3 to N5, narrowband light in which the magnitude relationship of absorbance is not reversed is irradiated, the U axis and the V axis are not perpendicular to each other. When the fifth narrowband light N5 having a wavelength of 400±10 nm, the absorbance coefficients of oxidized hemoglobin and reduced hemoglobin substantially become equal.

The blood vessel depth-oxygen saturation calculation section 124 specifies the oxygen saturation and the blood vessel depth corresponding to the first and second luminance ratios S1/S3 and S2/S3 calculated by the luminance ratio calculation section 120 on the basis of the correlation of the correlation storage section 122. The blood vessel depth-oxygen saturation calculation section 124 specifies corresponding coordinates (X, Y) in the luminance coordinate system 82 from the first and second luminance ratios S1/S3 and S2/S3 calculated by the luminance ratio calculation section 120 for a predetermined pixel in the blood vessel region, obtains the value on the UV coordinate system with the specified coordinates (X, Y) as coordinates on the blood vessel information coordinate system 83, and specifies coordinates (U, V). Thus, it is possible to obtain the blood vessel depth information U and the oxygen saturation information V for a pixel at a predetermined position in the blood vessel region.

Similarly to the oxygen saturation image generation section 118 of the first image processing section 106, the oxygen saturation image generation section 126 includes a color table (not shown) in which color information is allocated in accordance with the magnitude of the oxygen saturation. The oxygen saturation image generation section 126 specifies the color information corresponding to the oxygen saturation information V calculated by the blood vessel depth-oxygen saturation calculation section 124 from the color table.

If the color information is specified for all pixels in the blood vessel region, similarly to the oxygen saturation image generation section 118, the oxygen saturation image generation section 126 generates oxygen saturation image data in which the oxygen saturation of hemoglobin in the blood is reflected (pseudo-color display).

The blood vessel depth image generation section 128 includes a color table (not shown) in which color information is allocated in accordance with the degree of the blood vessel depth. In the color table, colors are allocated to be clearly distinguishable in accordance with the degree of the blood vessel depth, for example, blue when the blood vessel depth is the surface layer, green when the intermediate layer, and red when the deep layer. The blood vessel depth image generation section 128 specifies the color information corresponding to the blood vessel depth information U calculated by the blood vessel depth-oxygen saturation calculation section 124 from the color table.

If the color information is specified for all pixels in the blood vessel region, similarly to the oxygen saturation image generation section 118, the blood vessel depth image generation section 128 reads normal light image data of the normal observation image stored in the storage section 67, and reflects and superimposes the color information in and on read normal light image data, that is, synthesizes a color information image with the normal observation image to generate blood vessel depth image data in which the blood vessel depth information is reflected. The generated blood vessel depth image data is stored in the storage section 67 again. The color information may be reflected in each piece of component image data of each wavelength component or a synthesized image of the third to fifth narrowband light, instead of normal light image data.

When the blood vessel depth image is not required, the blood vessel depth image generation section 128 may not be provided.

Oxygen saturation image data and blood vessel depth image data generated by the second image processing section 108 are transmitted to the control section 65, and become an oxygen saturation image and a blood vessel depth image for endoscope observation together with various kinds of information in the control section 65. Then, the oxygen saturation image and the blood vessel depth image are switched by an image selector SW 17a of the input section 17, displayed on the display section 15 as detailed diagnostic images, and stored in the storage section 67, if necessary.

As described above, in the detailed diagnosis mode, image data of the respective narrowband light components are acquired using three kinds of narrowband light most suitable for calculating the oxygen saturation or the blood vessel depth in the second to fourth frames to calculate the oxygen saturation or the blood vessel depth. For this reason, while the frame rate is lowered, it is possible to calculate the oxygen saturation or the blood vessel depth accurately and with high precision. An image including the displayed blood vessel image information is a high-precision and accurate oxygen saturation image or blood vessel depth image, and is an image suitable for detailed diagnosis which allows detailed and accurate diagnosis of a lesion site or the like.

The control section 65 has a display control section 65a which causes the observation image based on image data subjected to the image process to be displayed on the display section 15 in each diagnosis mode, and a controller 65b which controls the respective sections of the endoscope 11, the light source device 12, and the processor 13.

The display control circuit 65a is used to read one image or a plurality of images from the storage section 67 and to display the read image on the display section 15. As an image display form, various patterns are considered. For example, a normal image may be displayed on one side of the display section 15, and an oxygen saturation image may be displayed on another side. A blood vessel depth image or an image representing the blood volume may be displayed. Of the oxygen saturation image, the blood vessel depth image, and the image representing the blood volume, one of the blood vessel depth image, the oxygen saturation image, and the information representing the blood volume selected by the image selector SW 17a (see FIG. 3) of the input section 17 may be displayed, or two or more images may be displayed. In the oxygen saturation image, for example, the blood vessel image representing low oxygen saturation can be displayed in cyan, the blood vessel image representing middle oxygen saturation can be displayed in magenta, and the blood vessel image representing high oxygen saturation can be displayed in yellow. In the blood vessel depth image, for example, the blood vessel image representing the surface layer blood vessel can be displayed in blue, the blood vessel image representing the intermediate layer blood vessel can be displayed in green, and the blood vessel image representing the deep layer blood vessel can be displayed in red.

The oxygen saturation, the blood vessel depth, the blood volume, and the like may be displayed on the display section 15 as linear images, such as character information.

As shown in Table 1, the controller 65b transmits a turn-on control signal of each light source to the light source control section 49 such that the light source control section 49 of the light source device 12 performs turn-on control of the narrowband light sources 41a and 41b of the first illumination light source section 41 and the narrowband light sources 43a to 43c of the second illumination light source section 43 in each frame in accordance with each diagnosis mode, thereby controlling the light source control section 49. The controller 65b transmits an imaging instruction signal to the imaging control section 62 such that the imaging control section 62 of the endoscope 11 allows imaging by the imaging element 21 in accordance with the turn-on of each light source by the light source control section 49 in each frame according to each diagnosis mode, thereby controlling the imaging control section 62.

The storage section 67 is constituted by a memory or a storage device, and stores image data of the captured image of each observation mode, image data of the oxygen saturation image generated by the image processing section 63, the blood vessel depth image, and the image representing the blood volume, and various kinds of data or programs necessary for driving, operation, control, and the like of the endoscope apparatus 10, particularly, the endoscope 11, the processor 13, the light source device 12, and the like.

Next, the function of an endoscope diagnosis apparatus of this embodiment will be described.

First, the function in the normal observation mode will be described.

An instruction of the observation mode or the like is input from the input section 17 of the endoscope apparatus 10 to the control section 65 of the processor 13, and the observation mode is set to the normal observation mode.

In the normal observation mode, the operation of the light source control section 49 of the light source device 12 is controlled by the control section 65 of the processor 13. Then, the narrowband light source 41a (LD445) of the first illumination light source section 41 of the system 1 is turned on, and the narrowband light sources 41b and 43a to 43c are turned off. Thus, excitation light E for normal observation is emitted from LD445.

In the endoscope 11, excitation light E for normal observation emitted from the light source device 12 is guided to the fluorescent substances 57 of the scope tip portion 35 by the optical fibers 55a and 55d. Thus, pseudo white light is emitted from the fluorescent substance 57 and irradiated from the illumination windows 37a and 37b onto the region to be observed of the subject. Then, reflected light from the region to be observed is condensed by the objective lens unit 39 and photoelectrically converted by the imaging element 21, and a captured image signal (analog signal) of a white light image is output.

The captured image signal (analog signal) of the white light image is converted to an image signal (digital signal) by the AFE 61, input to the image processing section 63, and subjected to the digital signal process by the DSP 64. Then, a predetermined image process suitable for a normal observation image is performed in accordance with the observation mode by the normal light image processing section 72, such that normal light image data is output. The normal observation image is displayed on the display section 15 on the basis of normal light image data by the control section 65.

Next, the operation in the special light observation mode will be described.

First, an instruction of the observation mode or the like is input from the input section 17 of the endoscope apparatus 10 to the control section 65 of the processor 13, and the observation mode is set to the screening diagnosis mode of the special light observation mode. Alternatively, the observation mode is switched from the normal light image mode to the screening diagnosis mode of the special light observation mode. If the special light observation mode is performed, information of the observation site, such as stomach, duodenum, or small intestine, at present is designated by an operation of the input section 17. Thus, in the oxygen saturation image generation sections 118 and 126 and the blood vessel depth image generation section 128, the color table according to the observation site is selected.

In the screening diagnosis mode, two frames constitute one set, and illumination light having a different irradiation pattern is irradiated in each frame.

First, in the first frame, as in the normal observation mode, the narrowband light source 41a (LD445) of the first illumination light source section 41 of the system 1 is turned on, and the narrowband light sources 41b and 43a to 43c are turned off. Then, excitation light E for normal observation is emitted from LD445, and an image signal of a captured image captured by the imaging element 21 is acquired, is digitalized by the AFE 61, and subjected to a digital signal process by the DSP 64 of the image processing section 63. Thus, white light RGB image data is obtained and stored in the storage section 67. Simultaneously, white light RGB image data is subjected to a predetermined image process suitable for a normal observation image by the normal light image processing section 102, such that normal light image data is output and stored in the storage section 67.

Subsequently, in the second frame, LD445 of the system 1 is turned off, the narrowband light source 41b (LD473) of the first illumination light source section 41 of the system 1 is turned on, and the narrowband light sources 43a to 43c are maintained in the turned-off state. Then, narrowband light N2 is emitted from LD473.

In the endoscope 11, narrowband light N2 from the light source device 12 is guided to the fluorescent substances 57 of the scope tip portion 35 by optical fibers 55a and 55d. Thus, synthesized light of most of narrowband light N2 having transmitted the fluorescent substances 57 and a small amount of fluorescence generated by the fluorescent substances 57 are irradiated onto the region to be observed of the subject from the illumination windows 37a and 37b.

Subsequently, as in the first frame, an image signal of a captured image captured by the imaging element 21 is acquired, digitalized by the AFE 61, and subjected to a digital signal process by the DSP 64 of the image processing section 63 to obtain RGB image data, which, if necessary, is stored in the storage section 67, and transmitted to the first image processing section 106 of the image processing section 63 of the special light image processing section 104.

Next, spectral estimation is performed using RGB image data obtained in the second frame by the spectral estimation section 110 of the first image processing section 106, such that 473 component image data is generated and transmitted to the luminance ratio calculation section 112.

Next, in the luminance ratio calculation section 112, white light G image data and white light R image data stored in the storage section 67 are read, and the blood vessel region including the blood vessel is specified from transmitted 473 component image data. Subsequently, with regard to the pixels at the same position in the blood vessel region, when the luminance value of the pixel of white light R image data is S1, the luminance value of the pixel of 473 component image data is S2, and the luminance value of the pixel of white light G image data is S3, the luminance ratio calculation section 112 obtains the first and second luminance ratios S1/S3 and S2/S3.

The first and second luminance ratios S1/S3 and S2/S3 obtained in the above-described manner are transmitted to the blood volume-oxygen saturation calculation section 116.

Subsequently, in the blood volume-oxygen saturation calculation section 116, information on the blood volume and the oxygen saturation corresponding to the first and second luminance ratios S1/S3 and S2/S3 is calculated on the basis of the correlation between the spectral luminance ratios S1/S3 and S2/S3 shows in FIG. 13, the blood volume, and the oxygen saturation stored in the correlation storage section 114. The information on the blood volume and the oxygen saturation calculated in the above-described manner is transmitted to the oxygen saturation image generation section 118.

Next, if the blood volume and the oxygen saturation are obtained, the oxygen saturation image generation section 118 specifies the color information corresponding to the oxygen saturation on the basis of the selected color table. For all pixels in the blood vessel region, the blood volume and the oxygen saturation are obtained, and the color information corresponding to the oxygen saturation is specified in the above-described sequence. When the oxygen saturation and the corresponding color information have been obtained for all pixels in the blood vessel region, the oxygen saturation image generation section 118 reads normal light image data of the normal observation image serving as a reference image from the storage section 67, and reflects the color information in the normal observation image to generate oxygen saturation image data. The generated oxygen saturation image data is stored in the storage section 67.

The control section 65 reads the oxygen saturation image data from the storage section 67, and pseudo-color displays the oxygen saturation image on the display section 15 on the basis of the read oxygen saturation image data.

In the above-described manner, in the endoscope apparatus 10, it is possible to accurately calculate information on oxygen saturation taking into consideration blood volume while reducing the influence of the depth of the blood vessel, and to display a smooth screening diagnostic image, in which the distribution of oxygen saturation is superimposed on the normal observation image as a pseudo color image, at a high frame rate so as to follow the movement of the endoscope 11.

Next, the observation mode is switched from the screening diagnosis mode of the special light observation mode to the detailed diagnosis mode.

In the detailed diagnosis mode, four frames constitute one set, and illumination light having a different irradiation pattern is irradiated in each frame.

First, in the first frame, as in the screening diagnosis mode, the narrowband light source 41a (LD445) of the first illumination light source section 41 of the system 1 is turned on, and the narrowband light sources 41b and 43a to 43c are turned off. Then, excitation light E for normal observation is emitted from LD445, and an image signal of a captured image captured by the imaging element 21 is acquired, digitalized by the AFE 61, and subjected to a digital signal process by the DSP 64 of the image processing section 63. Thus, white light RGB image data is obtained and stored in the storage section 67. Simultaneously, white light RGB image data is subjected to a predetermined image process suitable for a normal observation image by the normal light image processing section 102, such that normal light image data is output and stored in the storage section 67.

Subsequently, in the second frame, LD445 of the system 1 is turned off, the narrowband light source 43a (LD445) of the second illumination light source section 43 of the system 2 is turned on, and the narrowband light sources 41b and 43b to 43c are maintained in the turned-off state. Thus, narrowband light N3 is emitted from LD445 of the system 2.

In the endoscope 11, narrowband light N3 from the light source device 12 is guided to the optical deflection/diffusion members 58 of the scope tip portion 35 by the optical fibers 55b and 55c. Thus, narrowband light N3 whose light quantity is uniformized by the optical deflection/diffusion members 58 is irradiated onto the region to be observed of the subject from the illumination windows 37a and 37b.

Subsequently, as in the first frame, an image signal of a captured image signal captured by the imaging element 21 is acquired, digitalized by the AFE 61, and subjected to a digital signal process by the DSP 64 of the image processing section 63. Thus, 445 component image data is obtained and stored in the storage section 67.

Subsequently, in the third frame, LD445 of the system 2 is turned off, the narrowband light source 43b (LD473) of the system 2 is turned on, and the narrowband light sources 41a to 41b and 43c are maintained in the turned-off state. Thus, narrowband light N4 is emitted from LD473 of the system 2.

In the endoscope 11, as in the second frame, narrowband light N4 from the light source device 12 is guided to the scope tip portion 35 by the optical fibers 55b and 55c, and irradiated onto the region to be observed of the subject from the illumination windows 37a and 37b.

Subsequently, as in the second frame, an image signal of a captured image captured by the imaging element 21 is acquired, digitalized by the AFE 61, and subjected to a digital signal process by the DSP 64 of the image processing section 63. Thus, 473 component image data is obtained and stored in the storage section 67.

Subsequently, in the fourth frame, LD473 of the system 2 is turned off, the narrowband light source 43c (LD405) of the system 2 is turned on, and the narrowband light sources 41a to 41b and 43a are maintained in the turned-off state. Thus, narrowband light N5 is emitted from LD405 of the system 2.

In the endoscope 11, as in the third frame, narrowband light N5 from the light source device 12 is guided to the scope tip portion 35 by the optical fibers 55b and 55c, and irradiated onto the region to be observed of the subject from the illumination windows 37a and 37b.

Subsequently, as in the third frame, an image signal of a captured image captured by the imaging element 21 is acquired, digitalized by the AFE 61, and subjected to a digital signal process by the DSP 64 of the image processing section 63. Thus, 405 component image data is obtained and stored in the storage section 67. Simultaneously, 405 component image data is transmitted to the second image processing section 108 of the special light image processing section 104 of the image processing section 63.

Next, in the luminance ratio calculation section 120 of the second image processing section 106, 445 component image data, 473 component image data, and 405 component image data stored in the storage section 67 are read, and the blood vessel region including the blood vessel is specified from these pieces of component image data. Subsequently, with regard to the pixels at the same positions in the blood vessel region, when the luminance value of the pixel of 445 component image data is S1, the luminance value of the pixel of 473 component image data is S2, and the luminance value of the pixel of 405 component image data is S3, the luminance ratio calculation section 120 calculates the first and second luminance ratios S1/S3 and S2/S3.

The first and second luminance ratios S1/S3 and S2/S3 obtained in the above-described manner are transmitted to the blood vessel depth-oxygen saturation calculation section 124.

In the blood vessel depth-oxygen saturation calculation section 124, information on the oxygen saturation and the blood vessel depth corresponding to the first and second luminance ratios S1/S3 and S2/S3 is calculated on the basis of the correlation between the spectral luminance ratios S1/S3 and S2/S3 shown in FIG. 16, the oxygen saturation, and the blood vessel depth stored in the correlation storage section 122. The information on the oxygen saturation and the blood vessel depth calculated in the above-described manner is transmitted to the oxygen saturation image generation section 126 and/or the blood vessel depth image generation section 128.

Similarly to the oxygen saturation image generation section 118, if the oxygen saturation is obtained, the oxygen saturation image generation section 126 specifies the color information corresponding to the oxygen saturation on the basis of the selected color table. For all pixels in the blood vessel region, the oxygen saturation is obtained and the color information corresponding to the oxygen saturation is specified in the above-described sequence. If the oxygen saturation and the corresponding color information are obtained for all pixels in the blood vessel region, the oxygen saturation image generation section 126 reads normal light image data of the normal observation image serving as a reference image from the storage section 67, and reflects the color information in the normal observation image to generate oxygen saturation image data. The generated oxygen saturation image data is stored in the storage section 67.

If the blood vessel depth information is obtained, the blood vessel depth image generation section 128 specifies the color information corresponding to the blood vessel depth information on the basis of the selected color table. For all pixels in the blood vessel region, the blood vessel depth is obtained and the color information corresponding to the blood vessel depth is specified in the above-described sequence. If the color information is specified for all pixels in the blood vessel region, similarly to the oxygen saturation image generation section 118, the blood vessel depth image generation section 128 reads normal light image data of the normal observation image stored in the storage section 67, and reflects the color information in read normal light image data to generate blood vessel depth image data in which the blood vessel depth information is reflected. The generated blood vessel depth image data is stored in the storage section 67 again.

The control section 65 reads oxygen saturation image data and/or blood vessel depth image data from the storage section 67, and pseudo-color displays an oxygen saturation image and/or a blood vessel depth image on the display section 15 on the basis of read oxygen saturation image data and/or blood vessel depth image data.

As described above, in the endoscope apparatus 10, it is possible to accurately calculate the information on the oxygen saturation taking into consideration of the depth of the blood vessel, and to display a high-precision and accurate detailed diagnostic image in which the distribution of oxygen saturation is superimposed on the normal observation image as a pseudo color image.

Figure 17A:
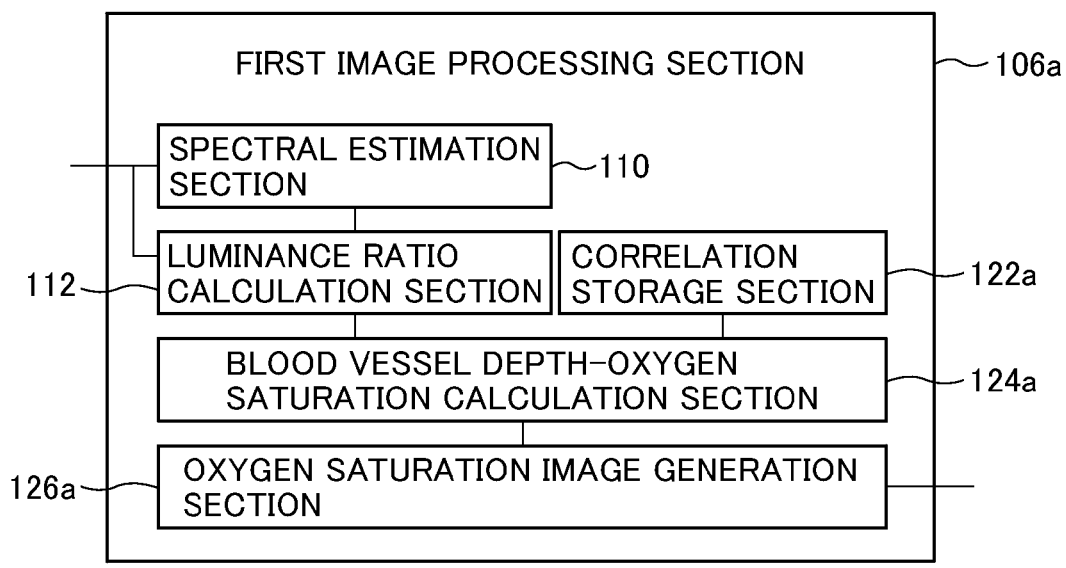
FIGS. 17A and 17B are block diagram showing the configuration of another example of a first image processing section and a second image processing section of a special light image processing section of an image processing section in the endoscope apparatus shown in FIG. 3.
Figure 17B:
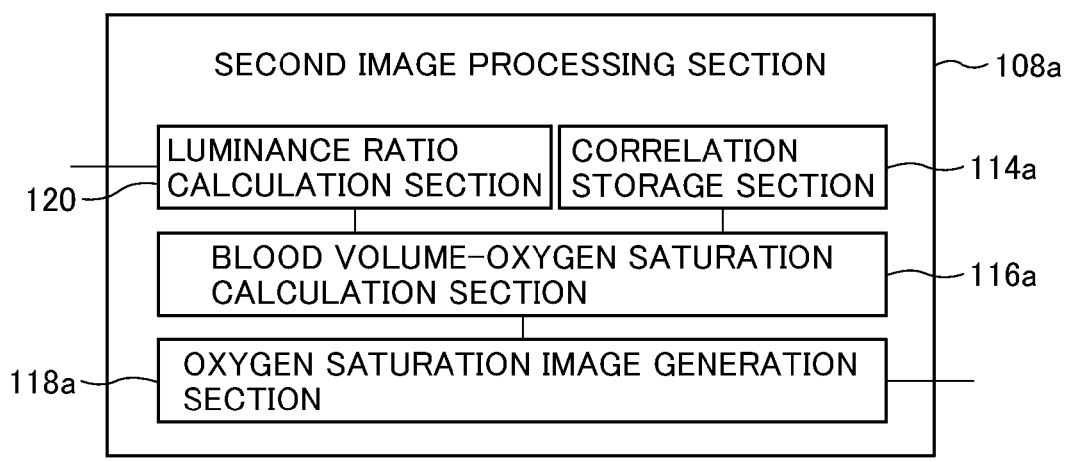

Although in the above-described example, the first image processing section 106 calculates the oxygen saturation from the correlation between the spectral luminance ratio (S1/S3 and S2/S3), the blood volume, and the oxygen saturation, and the second image processing section 108 calculates the oxygen saturation and the blood vessel depth from the correlation between the spectral luminance ratio (S1/S3 and S2/S3), the oxygen saturation, and the blood vessel depth, the invention is not limited thereto. As shown in FIG. 17A, the first image processing section 106a may calculate the oxygen saturation and the blood vessel depth from the correlation between the spectral luminance ratio (S1/S3 and S2/S3), the oxygen saturation, and the blood vessel depth. As shown in FIG. 17B, the second image processing section 108a may calculate the oxygen saturation from the correlation between the spectral luminance ratio (S1/S3 and S2/S3), the blood volume, and the oxygen saturation. The first image processing section 106 and the second image processing section 108a may calculate the oxygen saturation from the correlation between the spectral luminance ratio (S1/S3 and S2/S3), the blood volume, and the oxygen saturation. The first image processing section 106a and the second image processing section 108 may calculate the oxygen saturation and the blood vessel depth from the correlation between the spectral luminance ratio (S1/S3 and S2/S3), the oxygen saturation, and the blood vessel depth.

As shown in FIG. 17A, the first image processing section 106a has a spectral estimation section 110, a luminance ratio calculation section 112, a correlation storage section 122a, a blood vessel depth-oxygen saturation calculation section 124a, and an oxygen saturation image generation section 126a. The first image processing section 106a may have a blood vessel depth image generation section.

The spectral estimation section 110 and the luminance ratio calculation section 112 have the same configuration as those in the first image processing section 106.

The correlation storage section 122a, the blood vessel depth-oxygen saturation calculation section 124a, and the oxygen saturation image generation section 126a have the same configuration as the correlation storage section 122, the blood vessel depth-oxygen saturation calculation section 124, and the oxygen saturation image generation section 126 of the second image processing section 108, except that the values of the luminance values S1, S2, and S3 are the luminance value of the pixel of white light R image data, the luminance value of the pixel of 473 component image data, and the luminance value of the pixel of white light G image data, instead of the luminance value of the pixel of 445 component image data, the luminance value of the pixel of 473 component image data, and the luminance value of the pixel of 405 component image data. Thus, description thereof will not be repeated.

As shown in FIG. 17B, the second image processing section 108a has a luminance ratio calculation section 120, a correlation storage section 114a, a blood volume-oxygen saturation calculation section 116a, and an oxygen saturation image generation section 118a.

The luminance ratio calculation section 120 has the same configuration as that in the first image processing section 106.

The correlation storage section 114a, the blood volume-oxygen saturation calculation section 116a, and the oxygen saturation image generation section 118a have the same configuration as the correlation storage section 114, the blood volume-oxygen saturation calculation section 116, and the oxygen saturation image generation section 118 of the first image processing section 106, except that the values of the luminance values S1, S2, and S3 are the luminance value of the pixel 445 component image data, the luminance value of the pixel of 473 component image data, and the luminance value of the pixel of 405 component image data, instead of the luminance value of the pixel of white light R image data, the luminance value of the pixel of 473 component image data, and the luminance value of the pixel of white light G image data. Thus, description thereof will not be repeated.

Although the endoscope apparatus according to the invention has been described in detail in connection with various embodiments and examples, the invention is not limited thereto. It should be noted that various improvements or changes may be made without departing from the gist of the invention.

What is claimed is:

1. An endoscope apparatus comprising:
a first illumination light source section which individually emits broadband light and narrowband light for acquiring a special light image as a first illumination light;
a second illumination light source section which individually emits plural kinds of narrowband light having different emission wavelengths for acquiring the special light image as a second illumination light;
a light source control section which individually switches the broadband light and the narrowband light emitted individually from the first illumination light source section as the first illumination light and the plural kinds of narrowband light emitted individually from the second illumination light source section as the second illumination light;
an imaging element which individually receives return light from a subject, onto which at least two illumination lights from among the broadband light, the narrowband light and the plural kinds of narrowband light switched by the light source control section are individually irradiated, capturing an image for each imaging frame individually, and outputting an imaging signal of the image;
a special light image processing section which acquires the special light image as well as biological information relating to form and/or function of a biological object serving as the subject from the imaging signal captured by the imaging element; and
a controller which switches at least two diagnosis modes based on the biological information acquired by the special light image processing section,
wherein in order to acquire the special light image for acquiring one of the biological information, the broadband light and the narrowband light emitted from the first illumination light source section and the plural kinds of narrowband light emitted from the second illumination light source section are individually switched by the light source control section in accordance with the diagnosis mode switched by the controller, and the number of imaging frames by the imaging element for acquiring the special light image is varied, and
wherein said at least two diagnosis modes include a first diagnosis mode, and a second diagnosis mode in which a high-definition special light image having higher precision than the special light image acquired in the first diagnosis mode is acquired,
wherein the first diagnosis mode is a frame rate preference mode in which the frame rate is given preference over of the special light image so that a low-definition special light image is acquired by reducing the number of imaging frames processed per unit time to a number of imaging frame that is smaller than in the second diagnosis mode and increasing the frame rate to a frame rate that is higher than in the second diagnosis mode in order to acquire a low-definition special light image for acquiring the one of the biological information,
wherein the second diagnosis mode is a biological information preference mode in which a precision of the special light image for acquiring one of the biological information is given preference over the frame rate so that a high-definition special light image is acquired by increasing the number of imaging frames processed per unit time to a number of imaging frame that is greater than in the first diagnosis mode, and decreasing the frame rate to a frame rate that is smaller than in the first diagnosis mode,
wherein in the first diagnosis mode;
the light source control section controls so as to sequentially and alternately emit the broadband light and the narrowband light from the first illumination light source section, and
the imaging element individually receives the return light from a subject, onto which the broadband light and the narrowband light are individually irradiated, capturing two imaging frames, and outputting the imaging signals of the two imaging frames, and
the special light image processing section acquires the low-definition special light image as well as the one of the biological information from the imaging signals of the two imaging frames, and
wherein in the second diagnosis mode;
the light source control section controls so as to sequentially emit the broadband light as the first illumination light and the plural kinds of narrowband light as the second illumination light, and
the imaging element individually receives the return light from a subject, onto which the broadband light and the plural kinds of narrowband light are individually irradiated, capturing at least three imaging frames, and outputting the imaging signals of the at least three imaging frames, and
the special light image processing section acquires the high-definition special light image as well as the one of the biological information from the imaging signals of the at least three imaging frames,
wherein in case of acquiring the special light image for the one of the biological information, the number of imaging frames in the first diagnosis mode is two and smaller than at least three of the number of imaging frames in the second diagnosis mode, and
wherein the frame rate preference mode is a mode in which the subject is screened in a wide range by using the low-definition spatial light image in order to find a specific site of the subject of which the high-definition special light image needs to be obtained, and
wherein the biological information preference mode is a mode in which the high-definition special light image of the specific site of the subject specified by screening in the frame rate preference mode is obtained, and the biological information of the specific site of the subject is acquired.

2. The endoscope apparatus according to claim 1, wherein the broadband light and the narrowband light emitted from the first illumination light source section and the plural kinds of narrowband light emitted from the second illumination light source section are emitted from different illumination openings and illuminate the subject.

3. The endoscope apparatus according to claim 1,
wherein the first illumination light source section has
two or more narrowband light sources which individually emit plural kinds of narrowband light having different wavelengths, and
a fluorescent substance which transmits at least a part of plural kinds of narrowband light emitted from the two or more narrowband light sources, and is excited by one kind of narrowband light from one narrowband light source from among the two or more narrowband light sources to emit fluorescence,
the first illumination light source section emits from the fluorescent substance as the broadband light, synthesized light of transmitted light of the fluorescent substance by the one kind of narrowband light and the fluorescence emitted from the fluorescent substance,
the first illumination light includes the synthesized light as the broadband light and one or more kinds of another narrowband light from one or more narrowband light sources from among the two or more narrowband light sources, and
the second illumination light source section has two or more narrowband light sources which individually emit the plural kinds of narrowband light as the second illumination light.

4. The endoscope apparatus according to claim 1,
wherein the first illumination light source section has
first and second narrowband light sources which individually emit first and second narrowband light having different wavelengths, and
a fluorescent substance which transmits at least a part of the first and second narrowband light, and is excited by the first narrowband light to emit fluorescence,
the first illumination light source section emits synthesized light of the first narrowband light having transmitted through the fluorescent substance and the fluorescence emitted from the fluorescent substance excited by the first narrowband light, as the broadband light,
the second illumination light source section has three narrowband light sources which individually emit three kinds of narrowband light having different fluorescence wavelengths as the plural kinds of narrowband light,
the three narrowband light sources include fourth and fifth narrowband light sources which respectively emit the first and second narrowband light, and a third narrowband light source which emits third narrowband light having a wavelength different from the first and second narrowband light,
the first and fourth narrowband light sources are the same narrowband light source, and
the second and fifth narrowband light sources are the same narrowband light source different from the first and fourth narrowband light sources.

5. The endoscope apparatus according to claim 4,
wherein the first narrowband light is narrowband light which has a wavelength suitable for generating pseudo white light, as the broadband light when the fluorescence is excited and emitted from the fluorescent substance,
the second narrowband light is narrowband light which has a wavelength suitable for acquiring oxygen saturation of blood of the biological object as the biological information, and
the third narrowband light is narrowband light which has a wavelength suitable for acquiring information of a surface layer blood vessel of the biological object as the biological information.

6. The endoscope apparatus according to claim 4,
wherein the first and fourth narrowband light sources use the same first blue laser which emits narrowband light having a wavelength in a blue region as the first narrowband light,
the second and fifth narrowband light sources use the same second blue laser which emits narrowband light in a wavelength band from the blue region to a blue-green region longer than the emission wavelength band of the first blue laser, and
the third narrowband light source uses a third blue laser which emits narrowband light in a wavelength band from a blue-violet region to the blue region shorter than the emission wavelength band of the first blue laser.

7. The endoscope apparatus according to claim 6,
wherein the special light image processing section computes at least one of oxygen saturation of blood of the biological object, blood vessel information of the biological object, and blood volume information of the biological object.

8. The endoscope apparatus according to claim 4,
wherein the wavelength band of the first narrowband light is 440±10 nm, the wavelength band of the second narrowband light is 470±10 nm, and the wavelength band of the third narrowband light is 400±10 nm.

9. The endoscope apparatus according to claim 8,
wherein the special light image processing section computes at least one of oxygen saturation of blood of the biological object, blood vessel information of the biological object, and blood volume information of the biological object.

10. The endoscope apparatus according to claim 1,
wherein the imaging element is a color imaging element capable of separately imaging at least three wavelength bands.

11. The endoscope apparatus according to claim 1, further comprising:
a spectral estimation section which generates a narrowband image signal from the imaging signal captured by the imaging element at the time of the irradiation of the broadband light onto the subject by spectral estimation.

12. The endoscope apparatus according to claim 1,
wherein the special light image processing section computes at least one of oxygen saturation of blood of the biological object, blood vessel information of the biological object and blood volume information of the biological object.

13. The endoscope apparatus according to claim 12,
wherein the special light image processing section computes the oxygen saturation of blood of the biological object using correlation between a spectral luminance ratio of the imaging signal of the image and the oxygen saturation.

* * * * *